(12) United States Patent
Norenberg

(10) Patent No.: US 9,352,059 B2
(45) Date of Patent: *May 31, 2016

(54) NON-INVASIVE DIAGNOSTIC AGENTS AND METHODS OF DIAGNOSING INFECTIOUS DISEASE

(71) Applicant: STC.UNM, Albuquerque, NM (US)

(72) Inventor: Jeffrey P. Norenberg, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 63 days.

This patent is subject to a terminal disclaimer.

(21) Appl. No.: 14/093,260

(22) Filed: Nov. 29, 2013

(65) Prior Publication Data

US 2014/0086833 A1    Mar. 27, 2014

Related U.S. Application Data

(62) Division of application No. 12/991,253, filed as application No. PCT/US2009/003569 on Jun. 15, 2009, now Pat. No. 8,623,322.

(60) Provisional application No. 61/131,984, filed on Jun. 13, 2008.

(51) Int. Cl.
| | |
|---|---|
| *A61K 51/00* | (2006.01) |
| *A61M 36/14* | (2006.01) |
| *A61K 31/4178* | (2006.01) |
| *G01N 33/569* | (2006.01) |
| *A61K 51/04* | (2006.01) |

(52) U.S. Cl.
CPC .............. *A61K 51/00* (2013.01); *A61K 31/4178* (2013.01); *A61K 51/0453* (2013.01); *A61K 51/0497* (2013.01); *G01N 33/569* (2013.01); *A61K 51/044* (2013.01); *G01N 2333/70525* (2013.01); *G01N 2333/70553* (2013.01)

(58) Field of Classification Search
CPC ..................................................... A61K 51/00
USPC ....................................................... 424/1.11
See application file for complete search history.

(56) References Cited

U.S. PATENT DOCUMENTS

| 6,881,747 | B2 | 4/2005 | Larson et al. | |
|---|---|---|---|---|
| 8,097,237 | B2* | 1/2012 | Norenberg | A61K 51/0497 424/1.11 |
| 8,435,489 | B2* | 5/2013 | Norenberg et al. | 424/1.11 |
| 8,623,322 | B2* | 1/2014 | Norenberg | A61K 31/4178 424/1.11 |
| 8,834,838 | B2* | 9/2014 | Norenberg et al. | 424/1.11 |
| 2001/0034326 | A1 | 10/2001 | Larson | |
| 2007/0048216 | A1 | 3/2007 | Norenberg | |
| 2007/0183970 | A1 | 8/2007 | Goldenberg et al. | |
| 2007/0264265 | A1 | 11/2007 | Goldenberg et al. | |

OTHER PUBLICATIONS

Moshkowitz et al. (Nature 1971, 229, 422-424).*
Inghirami G, Wieczorek R, Zhu B.Y, et.al. Differential Expression of LFA-1 Molecules in Non-Hodgkin,s Lymphoma and Lyphoid Leukemia. Blood. 1988;72:1431-1434.
Horst E, Radaszkiewicz T, Pals ST, et.al. Expression of the leucocyte integrin LFA-1 (CD11a/CD18) and its ligand ICAM-1 (CD54) in lymphoid malignancies are related to lineage derivation and stage of differentiation but not to tumor grade. Leukemia. 1991 5(10):848-53.
Bechter OE, Eisterer W, Thaler J, et.al. Expression of LFA-1 identifies different prognostic subgroups in patients with advanced follicle center lymphoma (FCL). Leukemia Research. 1999;23(5):483-8.
Larson R.S, Davis T, Bolgna C, et.al. Dissociation of I Domain and global conformational changes in LFA-1: Refinement of small molecule-I domain structure-activity relationships. Biochemistry. 2005; 44:4322-4331.
Woska J.R, Shih D, Taqueti V.R, Hogg N, Kelly T.A and Kishimoto KT. A small-molecule antagonist of LFA-1 blocks a conformational change important for LFA-1 function. Journal of Leukocyte Biology. 2001;70:329-334.
Gursoy R.N. and Siahaan T.J. Binding and internalization of an ICAM-1 peptide by the surface receptors of T-cells. Journal of Peptide Research.1999;53:414-421.
Randi A.M. and Hogg Nancy. I Domain of β2 Integrin Lymphocyte Function-associated Antigen-1 Contains a Binding Site for Ligand Intercellular Adhesion Molecule-1. The Journal of Biological Chemistry.1994;269(17):12395-12398.
Kuriyama Y, Nakano M, Kawanishi Y and Toyama K. Cytofluorometric analysis of tumor cell size and follicle formation of B-cell lymphomas. Rinsho Ketsueki. 1995 36(4):279-285. [Jpn. J. Clin. Hematol. ;Japanese language only].
Petruzzelli L, Maduzia L and Springer T.A. Differential Requirements for LFA-1 Binding to ICAM-1 and LFA-1-Mediated Cell Aggregation. The Journal of Immunology.1998;160:4208-4216.
10. Buckley C.D, Ferguson E.D, Littler A.J, Bossy D and Simmons DL. Role of Ligands in the activation of LFA-1. European Journal of Immunology.1997;27:957-962.
Lub M, Kooyk Y and Figdor G.C. Ins and outs of LFA-1. Immunology Today. 1995;16(10):479-483.
Kelly T.A, Jeanfavre, Mcneil W.D, Woska R.J and et.al. Cutting edge: A small molecule antagonist of LFA-1 mediated cell adhesion. The Journal of Immunology. 1999; 163:5173-5177.

(Continued)

*Primary Examiner* — Michael G Hartley
*Assistant Examiner* — Melissa Perreira
(74) *Attorney, Agent, or Firm* — Henry D. Coleman; R. Neil Sudol

(57) ABSTRACT

The present invention is directed to novel non-invasive diagnostic tools to diagnose numerous infectious disease states or conditions. The present invention represents a clear advance in the art which presently relies on tissue biopsy for diagnoses of these disease states. The novel imaging probe is capable of detecting infected cells, as well tissue. This represents a quantum step forward in the diagnosis and staging of NHL using non-invasively molecular imaging techniques. This novel probe will also be useful to monitor patients response to therapeutic treatments and other interventions or therapies used in the treatment of these disease states or conditions. Compounds according to the present invention may be used as diagnostic tools for a number of conditions and diseases states as well as therapeutic agents for treating such conditions and disease states. Pharmaceutical compositions are also described.

33 Claims, 3 Drawing Sheets

(56) References Cited

OTHER PUBLICATIONS

Last-Barney K, Davidson W, Cardozo M, Frye LL, Grygon CA, Hopkins JL, Jeanfavre DD, Pav S, Qian C, Stevenson JM, Tong L, Zindell R, Kelly TA. Binding site elucidation of hydantoin-based antagonists of LFA-1 using multidisciplinary technologies: evidence for the allosteric inhibition of a protein—protein interaction. J Am Chem Soc. 2001;123(24):5643-5650.

Rocha M, Kruger A, Schirrmacher, et al. Dynamic Expression Changes In Vivo of Adhesion and Costimulatory Molecules Determine Load and Pattern of Lymphoma Liver Metastasis. Clinical Cancer Research. 1996;2:811-820.

Kang JH, Chung JK, Lee YJ, Shin JH, Jeong JM, Lee DS, Lee MC. Establishment of a human hepatocellular carcinoma cell line highly expressing sodium iodide symporter for radionuclide gene therapy. J Nucl Med. 2004;45 (9):1571-1576.

Norenberg JP, Krenning BJ, Konings IR, De Jong M, Garmestani K, Brechbeil MW, Atcher RW, Kusewitt DF, Garmestani K, Brechbiel MW, Kvols LK. Safety and efficacy of 213Bi-[DOTA0,Tyr3]octreotide (Bi-DOTATOC) in peptide receptor radionuclide therapy (PRRT) of neuroendocrine tumors in a preclinical model. Clinical Cancer Research; Nov. 2001;v7(11), suppl.S, p. 3732S. [Abstract #392].

Delcambre C, Reman O, Henry-Amar M, Peny AM, Macro M, Cheze S, et al. Clinical relevance of gallium-67 scintigraphy in lymphoma before and after therapy. Eur J Nucl Med 2000;27(2):176-184.

Johnston GS, Go MF, Benua RS, Larson SM, Andrews GA, Hubner KF, Gallium-67 citrate imaging in Hodgkin's disese: final report of cooperative group. J Nucl Med 1977;18(7):692-698.

Andrews GA, Hubner KF, Greenlaw RH. Ga-67 citrate imaging in malignant lymphoma: final report of cooperative group. J Nucl Med. 1978;19(9):1013-1019.

Hussain R, Christie DR, Gebski V, Barton MB, Gruenewald SM. The role of the gallium scan in primary extranodal lymphoma. J Nucl Med 1998;39(1):95-98.

Gallamini A, Biggi A, Fruterro A, Pugno F, Cavallero G, Pregno P, et al. Revisiting the prognostic role of gallium scintigraphy in low-grade non-Hodgkin's lymphoma. Eur J Nucl Med 1997;24(12):1499-1506.

Ben-Haim S, Bar-Shalom R, Israel O, Haim N, Epelbaum R, Ben-Shachar M, et al. Utility of gallium-67 scintigraphy in low-grade non-Hodgkin's lymphoma. J Clin Oncol 1996; 14(6):1936-1942.

Kumar R, Maillard I, Schuster SJ, Alavi A. Utility of fluorodeoxyglucose—PET imaging in management of patients with Hodgkin's and non-Hodgkin's lymphomas. Radiol Clin N Am 2004;42:1083-1100.

Macapinlac HA. The utility of 2-deoxy-2-[18F]fluoro-d-glucose-positron emission tomography and combined positron emission tomography and computed tomography in lymphoma and melanoma. Molecular Imaging and Biology 2004;6(4):200-2007.

Gross et al.; Science 1998, 281, 703-706.

Cimmino et al.; Annals of the Rheumatic Diseases 1992; 51:1007-1008.

Bedinghaus et al.; Am. Fam. Physician 2001; 64:791-796.

* cited by examiner

Chemical structure of $^{111}$In- DOTA-alkylamino-NorBIRT

NON-INVASIVE DIAGNOSTIC AGENTS AND METHODS OF DIAGNOSING INFECTIOUS DISEASE

RELATED APPLICATIONS

This application claims the benefit of priority of United States national stage patent application Ser. No. 12/991,253 filed Dec. 27, 2010 entitled "Non-Invasive Diagnostic Agents and Methods of Diagnosing Infectious Disease", which claims the benefit of priority of international patent application no. PCT/US2009/003569 filed Jun. 15, 2009, which claims the benefit of priority of U.S. provisional application Ser. No. 61/131,984 of identical title (as amended Aug. 19, 2008), filed Jun. 13, 2008, the entire contents of which three applications are incorporated by reference herein in their entirety.

FIELD OF THE INVENTION

The present invention is directed to diagnostic tools to image tissue suspected of or know to being infected, especially with a bacterial, fungal, viral, parasitic or other microbial pathogen. The present invention represents a clear advance in the art which presently relies on tissue biopsy for diagnoses of these disease states and conditions. The novel imaging probe is capable of detecting infected cells and tissue, as well as level of infection of the tissue. The present invention results in a significant advance and step forward in the diagnosis and treatment of infectious disease using the non-invasive molecular imaging techniques. Thus, in the present invention, the existence of a disease state may be diagnosed as well as the extent of disease. Accordingly, the present invention may be used to diagnose infections, including hard-to-diagnose infections and the assist in therapy of infections by monitoring therapy and the response of the disease to therapy. Compounds according to the present invention may be used as diagnostic tools for a number of conditions and diseases states as well as therapeutic agents for treating such conditions and disease states.

BACKGROUND OF THE INVENTION

A critical need exists to develop imaging agents which can diagnose and/or monitor infections in tissue in a patient. Currently, most imaging is based on the detection of mass infection or general metabolic activity. Imaging agents that elucidate the pathobiology of cells in the masses are lacking. An allosteric inhibitor of LFA-1 has been developed, the small molecule alkyl-amino-NorBirt. Determination of its structure activity relationship has permitted modifications allowing radiometal attachment through an alkylamino linker. We postulate that radiolabeled alkyl-amino-NorBirt will retain its binding affinity towards LFA-1 and thus can be used as a non-invasive imaging agent for a number of disease states and infections caused by microbial agents such as bacteria, viruses, fungi and parasites and other. Our previous work has demonstrated that the radiometal, [213]Bi, can be effectively incorporated into the alkyl-amino-NorBirt. We propose to link a radiometal with good imaging characteristics to image LFA-1 overexpression in infected tissues. The radiolabeled compound will allow imaging of infected cells, diagnosis and staging, as well as monitoring responses to other therapeutic interventions.

BACKGROUND AND SIGNIFICANCE

Lymphoma is a cancer of the lymphatics where the white blood cells start proliferating before they are fully mature and thus cannot function properly. These abnormal cells start collecting in the lymph nodes. The lymphoma cells can be either large or small and are usually grouped together to form small cell masses. Since leukocytes play the most vital role in immunological response by migrating to the site of injury through integrins and adhesion molecules, the chance of metastasis of lymphoma cells is very high.[1,2,3]

Integrins are α, β heterodimers whose activation leads to a change in structure and conformation which contribute to immune function.[4,5] One of the major membrane bound integrins receptors is $\beta_2$ integrin leukocyte function-associated antigen-1 (LFA-1), which is expressed by the leukocytes.[4,6,7] The α-subunit of LFA-1, has an N-terminally inserted domain (I-domain) that plays a central role in regulating ligand binding. LFA-1 receptors are expressed normally in all of the lymphoma cells and overly expressed on many lymphomas especially T-cell and B-cell neoplasms.[9,10,11,12] Also known as CD11A/CD18, LFA-1 plays a crucial role in many cellular and immunological processes (migration, antigen presentation, cytotoxicity, cell proliferation and haematopoiesis) by displaying both signaling and adhesive properties. This results in binding to the extracellular matrix as well as the receptors involved in cell-cell adhesion. This is regulated by binding to ligands such as intercellular adhesion molecules 1, 2 and 3 (ICAM-1, 2 & 3).[6,13]

LFA-1 must be activated to the extended high affinity form in order to mediate a stable adhesion with its ligand ICAM-1.[15] The resting state affinity of LFA-1 for the ICAM-1 is very low and is estimated at $10^{-15}$-$10^{-6}$ M for mice.[16] Binding of the activated LFA-1 with the ICAM-1 through its I-domain (which retains its function as an isolated protein fragment) results in cell adhesion and migration along with intracellular signals which may cause cytotoxic action, cell proliferation or apoptosis.[6]

Development of allosteric LFA-1 inhibitors can cause inhibition of early events like the cell-cell as well as cell-extra cellular matrix adhesion and will prevent metastasis of lymphoma cells.5,7,17

Recently small molecules have been developed that bind to the I-domain of the α-subunit of LFA-1 receptors and stabilize it to the low affinity state. Structure activity studies of one of such molecule, BIRT-377, suggest that it binds to LFA-1 solely through nonionic interaction. (*J Am Chem Soc* 123, 5643-5650). Two hydrophobic pockets of the I-domain and the aromatic rings of Birt-377 interact with each other in an edge-to-face aromatic/aromatic orientation. This binding presumably prevents displacement of the overall conformational changes of the whole protein stabilizing it in the bent, low affinity state. Many derivatives of BIRT-377 have been developed. One of them is alkylamino-NorBirt. Studies have demonstrated that this derivative retains its affinity as the original DOTA-alkylamino-NorBirt. Even in the presence of divalent cations like Mn++ (which results in activation and small conformational changes in the I-domain), BIRT-377 and its derivative (the alkylamino-NorBirt) inhibit the ligand binding by stabilizing LFA-1 in the bent, low affinity state.[5] Thus, it prevents the ICAM-1 adhesion on LFA-1 and thereby prevents the leukocytes from migration (metastasis).[20] It also inhibits the intercellular signals (outside-in signaling) and hence affects the functional activity of cell.

Structure activity work with BIRT-377 had suggested that the hydantoin methyl group when bound to LFA-1 was oriented away from the binding site, suggesting that changes at this site would not interfere with BIRT-377 binding. The modification of Birt-377 allows a linker 1,4,7,10-tetraazacyclododecane-1,4,7,10-tetraacetic acid (DOTA) to be attached to the alkylamino chain resulting in DOTA-alkylamino-Nor- Birt. A radiometal then can be incorporated in the DOTA linker for non-invasive imaging.

There are several characteristics of Lymphoma cells and the LFA-1 receptors, which make them amenable for non-invasive imaging. They are:

The lymphoma cells grow in masses

All types of lymphoma express LFA-1 receptors

In many cases and types, the LFA-1 receptors are over expressed

Non-Haematopoetic cells do not express LFA-1 receptors

Currently very crude techniques are available for non-invasive imaging of lymphomas.

Thus the radiolabeled DOTA-alkylamino-NorBirt can potentially be used, as a non-invasive imaging tool for lymphomas.

The need for non-invasive imaging in lymphoma is very important. The current methods of staging and detecting the residual disease are very crude. Since the research is still in its early stages, we do not expect to achieve immediate diagnostic capabilities. However, detecting the residual disease after therapy and increasing the sensitivity of staging the disease can be accomplished. The advantage of this non-invasive imaging is the sensitivity with which the radiopharmaceutical can detect the disease and its spread in the body.

BRIEF DESCRIPTION OF THE INVENTION

Figure 1:
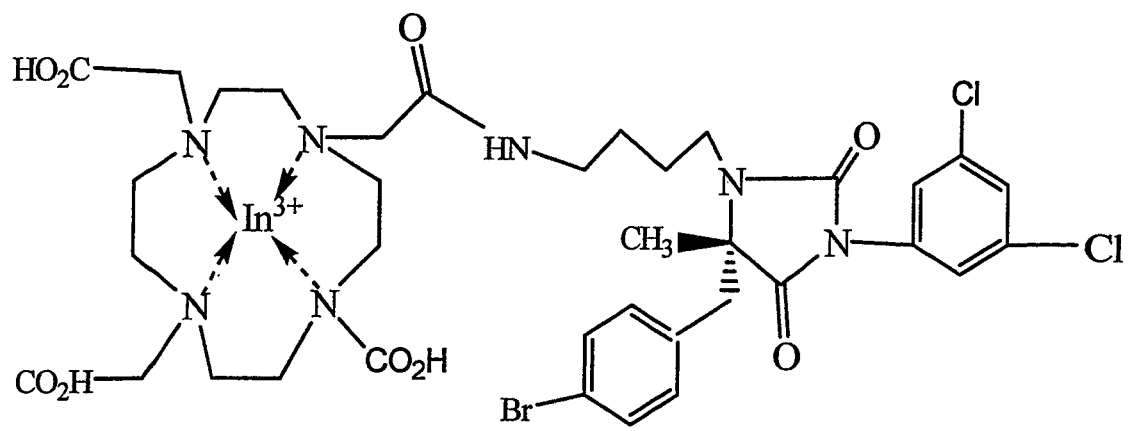
FIG. 1 shows the chemical structure of $^{111}$In-DOTA-alkylamino-NorBIRT.
Figure 2:
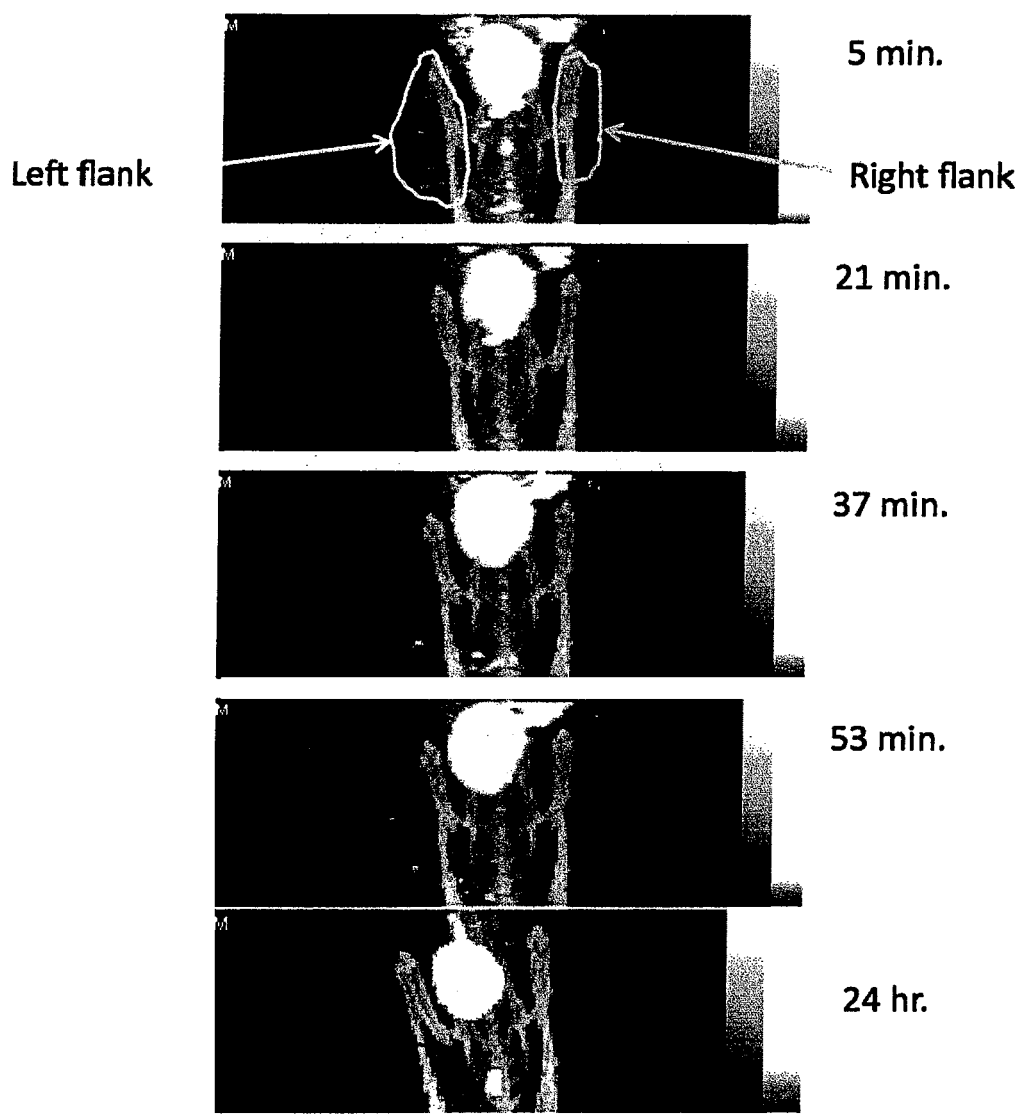
FIG. 2 shows SPECT/CT Images of a 15-week old, male C57Blk6 mouse injected with $^{111}$In-alkylaminoNorBIRT intravenously, 18 hours following inoculation with ~5×10$^8$ E. coli cells in the muscle overlying the proximal left hind leg.
Figure 3:
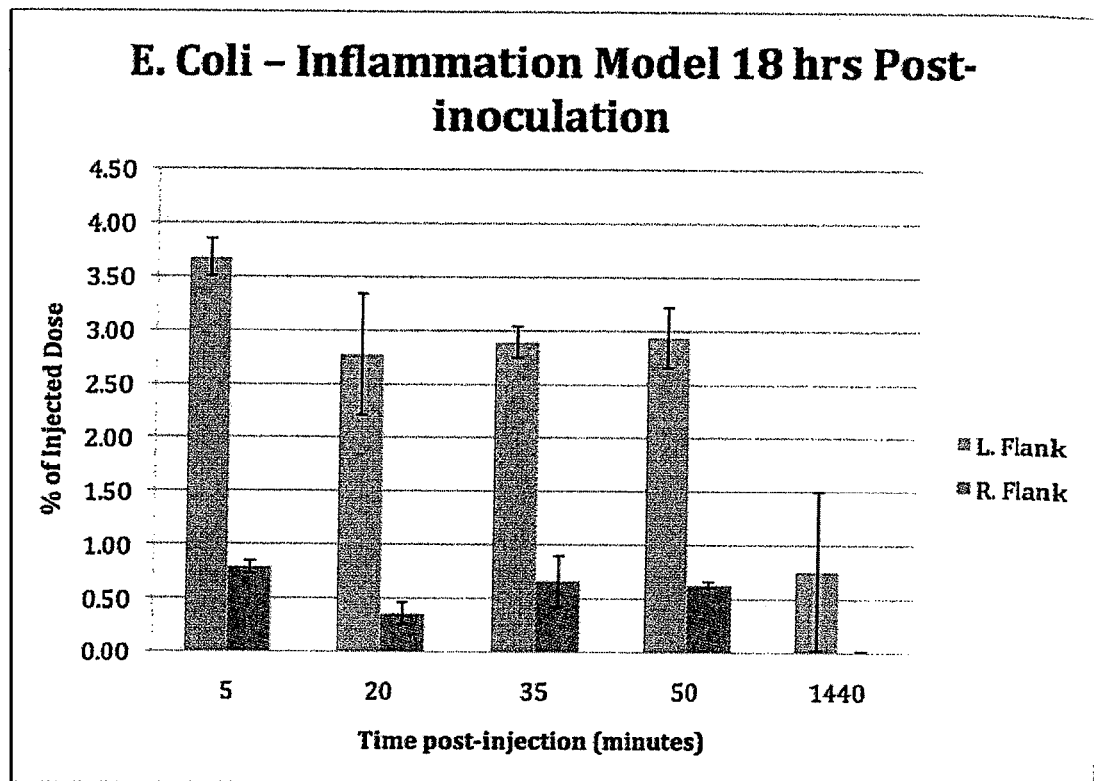
FIG. 3 shows the biodistribution data from C57Blk6 mouse injected with $^{111}$In-alkylaminoNorBIRT intravenously 18 hours following inoculation with ~5×10$^8$ E. coli cells.

In the present invention, an agent for imaging infected or inflamed tissues, in particular tissue infected with a variety of bacteria, viruses, fungi and parasites (infectious disease) or tissues responding to inflammation signals are disclosed. Compounds of the present invention have the chemical formula I:

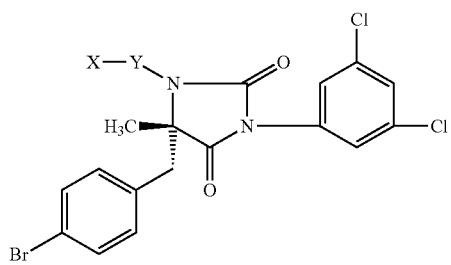

Where Y is a chemical linker which links the nitrogen to a chelate group or tricarbonyl complex X, wherein X incorporates or complexes with a radioisotope. In preferred aspects of the invention, Y is an optionally substituted $C_1$-$C_{10}$ hydrocarbyl (including an optionally substituted aryl group), preferably an optionally substituted alkyl group, for example a —$(CH_2)_n$Z— group, where n is from 1 to 6 and Z is O, NR or N(R)—$CH_2CH_2$—O, where R is H or a $C_1$-$C_3$ alkyl (preferably H) or Z is a keto (C=O) group, a $S(O)_w$ group where w is from 0 to 4 (i.e., a sulfide, sulfoxide, sulfone, sulfonate or sulfate group), a phosphonate group or a phosphate group and X is a chelate group in which a radioisotope is incorporated or complexed. In certain preferred aspects, Y is a —$(CH_2)_n$NH— group, where n is from 1 to 6, preferably from 2 to 4, preferably 4 and X is a polyaminocarboxylic macrocycle, preferably 1,4,7,10-tetraazacyclododecane-1,4,7,10-tetraacetic acid (DOTA).

In other aspects of the invention, Y is a linker comprising a $C_1$-$C_{10}$, preferably a $C_3$-$C_8$ substituted hydrocarbyl group (which is bonded to the nitrogen of the dioxoimidazolyl group through a keto group) containing two amino groups or two sulfur groups which are linked with the tricarbonyl compound X which incorporates or complexes to the radioisotope. In certain aspects, the preferred linker contains a dithiahexyl group or a diaminohexyl or diaminobutyl group. In another aspect, the linker may be derived from lysine (linked to the dioxoimidazolinyl group through the carboxylic acid moiety of lysine). Chemical linkage of the linker to the dioxoimidazolinyl group may be through a carbonyl group, alkylene group or other group capable of being linked to the nitrogen of the dioxoimidazolinyl group.

Preferred compounds according to the present invention are represented by the chemical structure:

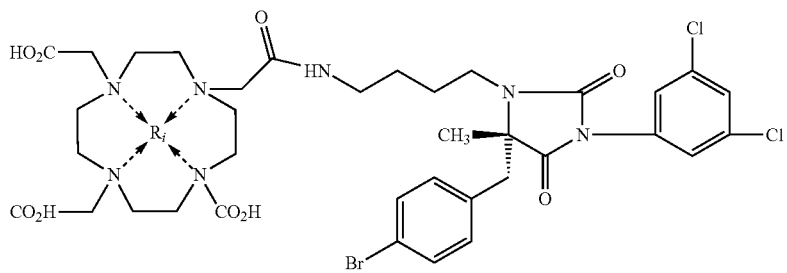

Where Ri is a radioisotope as otherwise described herein below, more preferably $^{213}$Bi, $^{177}$Lu, $^{68}$Ga, $^{67}$Ga, or $^{111}$In. In particularly preferred aspects, Ri are $^{111}$In ($^{111}$In$^{3+}$) or $^{68}$Ga ($^{68}$Ga$^{3+}$). It is noted that compounds according to the present invention exhibit a favorable bioavailability to tissues which have been infected with a microbial infection, thus providing a ready means by which the infection may be diagnosed and/or monitored for therapeutic success or failure. This favorable bioavailability is also evidenced in inflamed tissues such as those observed in acute and chronic inflammatory conditions such as arthritis, inflammatory bowel and Crohn's disease, cardiovascular diseases, and neurological diseases.

Radioisotopes are selected based on the physical half life, the decay mode (alpha, beta, auger, gamma, X-ray) and the energy of the radioisotope. Exemplary radioisotopes for use in the present invention include, for example, $^{90}$Y, $^{111}$In, $^{177}$Lu, $^{225}$Ac, $^{209}$Bi, $^{213}$Bi, $^{67}$Ga, $^{68}$Ga, $^{64}$Cu, $^{67}$Cu, $^{71}$As, $^{72}$As, $^{76}$As, $^{77}$As, $^{65}$Zn, $^{76}$Br, $^{48}$V, $^{49}$V, $^{203}$Pb, $^{209}$Pb, $^{212}$Pb, $^{166}$Ho, $^{153}$Pm, $^{201}$Tl, $^{188}$Re, $^{186}$Re, $^{99m}$Tc. In certain aspects of the present invention, preferred radioisotopes include, for example, $^{213}$Bi, $^{177}$Lu, $^{111}$In, $^{68}$Ga, more preferably, $^{68}$Ga and $^{111}$In, among others. $^{111}$In and, $^{68}$Ga are preferred for use in the present invention because the incorporation of this radioisotope into the basic chemical structure results in a compound having favorable bioavailability characteristics after administration to a patient. Many radioisotopes are used in the present invention preferably in cationic form.

Methods of diagnosing or treating diseases or conditions, especially infectious or inflammatory diseases or conditions which occur as a consequence of an infectious disease in a patient in need thereof, are another aspect of the invention. In this method, an effective amount of one or more compounds according to the present invention is administered to a patient in need thereof to diagnose a condition or disease state or to treat or assess the treatment of the condition or disease state. Disease states or conditions which may be diagnosed or treated by the present invention include, for example:

1. Skin and soft tissue infections such as: folliculitis, furuncles, and carbuncles; erysipelas; lymphangitis; cellulitis, necrotizing soft tissue infections, diabetic foot infections, decubitus ulcers
2. Bone and joint infections such as: osteomyelitis, infectious arthritis, mastoiditis
3. Central nervous system infections arising from meningococcal, pneumococcal, diplococcal, *H. influenzae*, as well as other gram-negative and gram-positive bacterium, mycobacterium tuburculosis, *Cryptococcal neoformans*, or viral encephalitis
4. Upper and lower respiratory tract infections such as: bronchitis, bronchiolitis, pneumonia, otitis media, pharyngitis, sinusitis, epiglottitis and laryngitis
5. Infective endocarditis
6. Tuberculosis
7. Gastrointestinal infections such as: enterotoxigenic, enterhemorrhagic, and travelers diarrhea; pseudomembranous colitis; Shigelloisis; Salmonellosis; Campylobacteriosis; Yersiniosis; gastroenteritis
8. Intra-abdominal infections of the stomach, biliary tract, proximal small-bowel, distal ileum, and colon; primary and secondary bacterial peritonitis; abscess; appendicitis; cholysystitis, cholangitis, contamination from abdominal trauma, pelvic inflammatory disease
9. Parasitic diseases, including protozoan infections, diseases from roundworms and flatworms (helminthiasis) and other endoparasites, among others
10. Urinary tract infections, prostatitis, urethritis, epididymitis, cervicitis or vulvovaginitis, proctitis, salpingitis
11. Sepsis and septic shock
12. Superficial and invasive fungal infections such as: histoplasmosis, blastomycosis, coccidioidomycosis, cryptococcosis, Candidiasis, Apergillosis
13. Post-surgical infections
14. Fever of unknown origin
15. Cardiovascular diseases such as cardiovascular ischemia, coronary atherosclerosis, angina, and heart failure
16. Degenerative joint diseases including osteoarthritis (degenerative joint disease) as a result of trauma to the joint, infection of the joint, or age; rheumatoid arthritis and psoriatic arthritis and/or autoimmune diseases in which the body attacks itself. Septic arthritis caused by joint infection. Gouty arthritis caused by deposition of uric acid crystals in the joint, causing inflammation
17. Bursitis inflammation of one or more bursae (small sacs) of synovial fluid in the body.
18. Diseases resultant from vascular disease or injury from atherosclerosis, ischemia, or infarct including: stroke, cerebrovascular ischemia, cerebrovascular infarct, cerebrovascular accidents, myocardial ischemia and infarct
19. Gastrointestinal inflammatory conditions such as peptic and duodenal ulcer disease, inflammatory bowel and Crohn's disease, toxic megacolon, colangeous colitis, lymphocytic colitis, ischemic colitis, diversion colitis, Behcet's colitis, inflammatory colitis In the diagnostic method according to the present invention, a compound according to the present invention is administered to a patient. Evidence of a disease state or condition of the tissue to be diagnosed and its relevance to disease (for example, from elevated expression of LFA-1/CAM receptors) in tissue of said patient is made through standard well-known nuclear imaging techniques, especially radiation (radionuclide) imaging, including scintigraphic imaging, in which an image(s) taken from a patient is/are compared to a standard, which may be an image from normal, uninfected tissue or an image or images from infected tissue at various stages of infection, is indicative of a disease state or condition in the tissue of the patient. In general, elevated levels of radiation emanating from a diagnosed tissue is evidence of elevated LFA-1/CAM receptor activity and indicative of a disease state or condition wherein these receptors are found at elevated levels and a disease state or condition occurs. It has recently been discovered that the present method is applicable to a large number of infectious diseases states which are caused by microbial agents, including bacteria, viruses, fungi and protozoa, as well as multicellular parasites (helminthic and other endoparasites). Thus, the present invention may be used to diagnose the existence and/or severity of a disease state, as well as response of a disease state or condition to therapy. This is done by imaging tissue which is infected or suspected of being infected to develop one or more images and then comparing the image(s) with a standard image or images from normal tissue and/or infected tissue.

Pharmaceutical compositions according to the present invention include an effective amount of one or more compounds according to the present invention optionally in combination with a pharmaceutically acceptable carrier, additive or excipient. Additional pharmaceutical compositions comprise an effective amount of at least one compound according to the present invention, in combination with an effective amount of at least one additional active agent (e.g., an anti-cancer agent or an anti-microbial agent such as an antibacterial agent, an antiviral agent, an antifungal agent an antiprotozoal agent, an antihelminthic agent), optionally in combination with a pharmaceutically acceptable carrier, additive or excipient.

Another aspect of the invention relates to a method for reducing the likelihood or preventing a disease state or condition in a patient at risk for a disease state or condition or who likely will succumb to one or more of the above-described disease states comprising administering to said patient an effective amount of one or more compounds/pharmaceutical compositions according to the present invention. Treatment of or monitoring of treatment of diseases/infections in tissues (which may also be diagnosed by the present methods) by methods according to the present invention represent further aspects. This method optionally comprises the step of modifying treatment of said disease state or condition in the event that the monitoring evidences that therapy should be modified.

Thus, the present invention relates to a method for diagnosing an infection (infectious disease) in a patient comprising administering to said patient an effective amount of a compound as generally described hereinabove to a patient suspected of or at risk for being infected and then diagnosing the existence of a disease or condition in said patient by imaging said patient and determining the existence of an imaging (radioimage) signal from tissue in said patient consistent with the existence of a disease state or condition. The method comprises comparing the image(s) obtained from the patient to one or more standard images (e.g. a standard for normal tissue and/or of diseased tissue). A determination that tissue or an organ in a patient is infected and the extent and/or severity of infection is made by comparing the image from the tissue or organ suspected of being infected with the standard image. If the image from the tissue is significantly higher than a standard image from non-infected tissue, then a diagnosis that the tissue is infected may be made. Alternatively, if the image from the tissue is approximately the same as a standard image from infected tissue, then a diagnosis that the tissue is infected and the severity of infection may be made.

A particularly preferred group of compounds for use in the present invention are compounds according to the chemical structure:

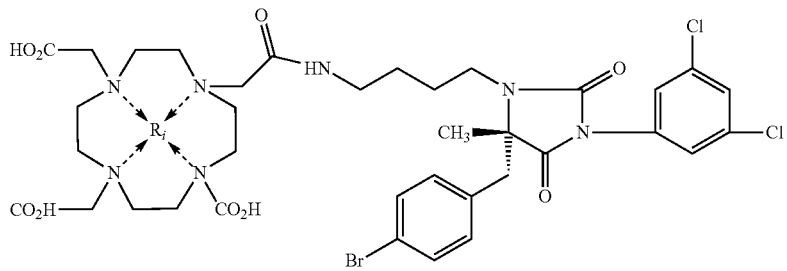

Where Ri is a radioisotope as otherwise described hereinbelow, more preferably $^{213}$Bi, $^{177}$Lu, $^{68}$Ga or $^{111}$In, including pharmaceutically acceptable salts thereof. In particularly preferred aspects, Ri are $^{68}$Ga or $^{111}$In according to the following chemical structure (or a pharmaceutically acceptable salt):

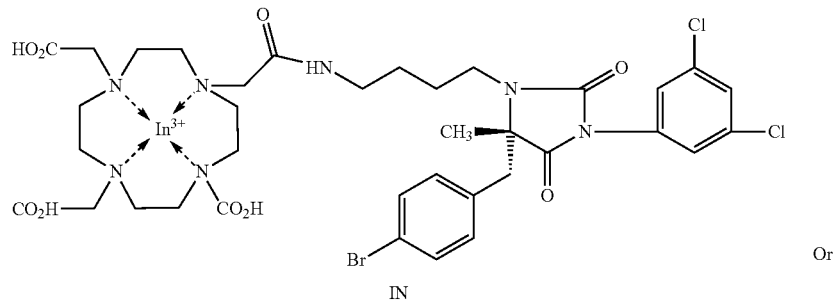

IN

Or

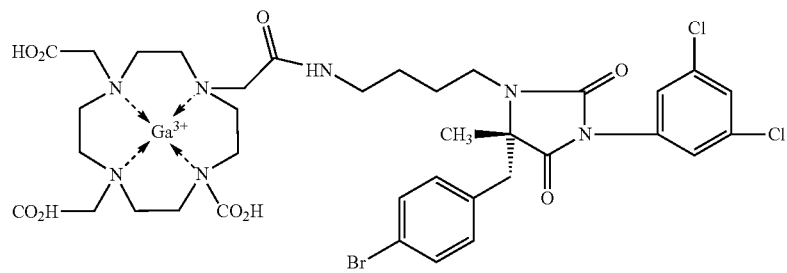

It is noted that compounds according to the present invention (and in particular, compound IN) exhibit a favorable bioavailability to tissues which have been infected with a microbial infection, thus providing a ready means by which the infection may be diagnosed and/or monitored for therapeutic success or failure.

In alternative embodiments, administration of compounds according to the present invention assist in monitoring therapies for treating an infection wherein during treatment of an infection, a compound according to the present invention may be administered to a patient such that infected tissue may be imaged/monitored and optionally/preferably compared to a standard image (from uninfected tissue and/or infected tissue) in order to determine the effect of therapy on the diseased tissue. The therapy may thereafter be terminated because a cure has been effected, the same therapy may be continued to further treat the infection, or the therapy may be modified in order to further treat the infection.

In the present method, the following infectious disease states, generally microbial (e.g., bacterial, fungal, viral) and/or parasitic infections, among others, may be diagnosed, monitored and/or treated:

1. Skin and soft tissue infections such as: folliculitis, furuncles, and carbuncles; erysipelas; lymphangitis; cellulitis, necrotizing soft tissue infections, diabetic foot infections, decubitus ulcers
2. Bone and joint infections such as: osteomyelitis, infectious arthritis, mastoiditis
3. Central nervous system infections arising from meningococcal, pneumococcal, diplococcal, *H. influenzae*, as well as other gram-negative and gram-positive bacterium, mycobacterium tuberculosis, *Cryptococcal neoformans*, or viral encephalitis
4. Upper and lower respiratory tract infections such as: bronchitis, bronchiolitis, pneumonia, otitis media, pharyngitis, sinusitis, epiglottitis and laryngitis
5. Infective endocarditis
6. Tuberculosis
7. Gastrointestinal infections such as: enterotoxigenic, enterhemorrhagic, and travelers diarrhea; pseudomembranous colitis; Shigelloisis; Salmonellosis; Campylobacteriosis; Yersiniosis; gasteroenteritis
8. Intra-abdominal infections of the stomach, biliary tract, proximal small-bowel, distal ileum, and colon; primary and secondary bacterial peritonitis; abscess; appendicitis; cholysystitis, cholangitis, contamination from abdominal trauma, pelvic inflammatory disease
9. Parasitic diseases, including protozoan infections, diseases from roundworms and flatworms (helminthiasis) and ectoparasites (pediculosis, acariasis), among others
10. Urinary tract infections, prostatitis, urethritis, epididymitis, cervicitis or vulvovaginitis, proctitis, salpingitis
11. Sepsis and septic shock
12. Superficial and invasive fungal infections such as: histoplasmosis, blastomycosis, coccidioidomycosis, cryptococcosis, Candidiasis, Apergillosis
13. Post-surgical infections
14. Fever of unknown origin
15. Cardiovascular diseases such as cardiovascular ischemia, coronary atherosclerosis, angina, and heart failure
16. Degenerative joint diseases including osteoarthritis (degenerative joint disease) as a result of trauma to the joint, infection of the joint, or age; rheumatoid arthritis and psoriatic arthritis and/or autoimmune diseases in which the body attacks itself. Septic arthritis caused by joint infection. Gouty arthritis caused by deposition of uric acid crystals in the joint, causing inflammation
17. Bursitis inflammation of one or more bursae (small sacs) of synovial fluid in the body.
18. Diseases resultant from vascular disease or injury from atherosclerosis, ischemia, or infarct including: stroke, cerebrovascular ischemia, cerebrovascular infarct, cerebrovascular accidents, myocardial ischemia and infarct
19. Gastrointestinal inflammatory conditions such as peptic and duodenal ulcer disease, inflammatory bowel and Crohn's disease, toxic megacolon, colangeous colitis, lymphocytic colitis, ischemic colitis, diversion colitis, Behcet's colitis, inflammatory colitis Preparation of compounds according to the present invention proceeds using standard synthetic chemical techniques which are readily available in the art. Synthetic methods for obtaining compounds related to the present invention may be found in U.S. Pat. No. 6,881,747, issued Apr. 19, 2005, which is incorporated by reference herein. These methods can serve as guides for obtaining compounds according to the present invention. In general, the present compounds may be made by condensing a chelate compound to which is bound a radionuclide onto an activated moiety containing either an electrophilic group or a nucleophilic group of a linker group which is chemically linked to the amine of the dioxoimidazolidine group of the compounds according to the present invention. Alternatively, the chelate may be first reacted with one end of a difunctional chemical linker and the unreacted moiety of the linker group may thereafter be reacted with the dioxoimidazoline group. Radioisotopes may be added (chelated) to the compound at an early or later stage in the chemical synthetic method.

As discussed above, tricarbonyl complexes may be used to prepare the final diagnostic/therapeutic compound according to the present invention. Preparation of the compound can also be prepared using Technetium (I) and Rhenium (I) tricarbonyl complexes such as those listed below using methods described by H.-J. Pietzsch, A. Gupta, M. Reisgys, A. Drews, S. Seifert, S. Seifert, et. al. [Chemical and Biological Characterization of Technetium(I) and Rhenium(I) Tricarbonyl Complexes with Dithioether Ligands Serving as Linkers for Coupling the Tc(CO)$_3$ and Re(CO)$_3$ Moieties to Biologically Active Molecules, *Bioconjugate Chem.*, 11(3) 414-424, 2000].

Bromo(3,6-dithiaoctane-S,S)tricarbonylrhenium(I)]
[Bromo(4,7-dithia-1-octyne-S,S)tricarbonylrhenium(I)]
[Bromo(1-carboxy-3,6-dithiaheptane-S,S)tricarbonylrhenium(I)] ($C_9H_{12}BrO_5ReS_2$)
[Bromo(1,6-dicarboxy-2,5-dithiahexane-S,S)tricarbonylrhenium(I)] ($C_9H_{10}BrO_7ReS_2$)
[1-Carboxylato-3,6-dithiaheptane-O,S,S)tricarbonylrhenium(I) ($C_9H_{11}O_5ReS_2$)
[(1-Carboxylato-6-carboxy-2,5-dithiahexane-O,S,S)tricarbonylrhenium(I)] ($C_9H_9O_7ReS_2$)
[Bromo(1,8-dihydroxy-3,6-dithiaoctane-S,S)tricarbonylrhenium(I)] ($C_9H_{14}BrO_5ReS_2$)
[(1,8-Dihydroxy-3,6-dithiaoctane-O,S,S)tricarbonylrhenium(I)]nitrate ($C_9H_{14}NO_8ReS_2$)
[Chloro(3,6-dithiaoctane-S,S)tricarbonyltechnetium(I)]
[Chloro(4,7-dithia-1-octyne-S,S)tricarbonyltechnetium(I)]
[Chloro(1-carboxy-3,6-dithiaheptane-S,S)tricarbonyltechnetium(I)]
[Chloro(1,6-dicarboxy-2,5-dithiahexane-S,S)tricarbonyltechnetium(I)]
[1-Carboxylato-3,6-dithiaheptane-O,S,S)tricarbonyltechnetium(I)
[(1-Carboxylato-6-carboxy-2,5-dithiahexane-O,S,S)tricarbonyltechnetium(I)]

The tricarbonyl complexes as described above may be reacted with the dioxoimidazoinyl compound to form a chemically linked tricarbonyl complex which contains the radioisotope.

Attachment of metal radioisotopes to the compounds prepared above make the final NorBirt diagnostic/therapeutic compounds. Analogous preparations yield compounds containing other radioisotopes as otherwise disclosed herein.

Linkers:

The linkers are comprised of alkyl chains of various lengths and containing various side chains (optionally substituted) depending on the hydrophobic/hydrophilic properties of the final product and the clinical needs. Linkers preferably contain O, S or NH or other functional group on the distal end of the molecule in order to attach a chelate to which may be bound a radioisotope. Simple condensation or other reactions may be used to covalently link the linker to the chelate so that a radionuclide may be complexed accordingly.

Chelates:

Are selected based on the metal to be incorporated and the clinical objectives.

Chelates selected is such as those listed above and include Open-Chain Polyaminocarboxylates; AZA Macrocyclics; Polyaminocarboxylic Macrocycles; and Polyaminophosphonate Macrocycles.

Chelates for inclusion in the present application are selected based on the metal to be incorporated and the clinical objectives. Chelates selected for use in the present invention include those listed below.

Open-Chain Polyaminocarboxylates:
edta: ethylenediaminetetraacetic acid
dtpa: diethylenetriaminepentaacetate
AZA Macrocyclics
cyclen: 1,4,7,10-tetraazacyclododecane
cyclam: 1,4,8,11-tetraazacyclotetradecane
bridged-cyclam: 1,4,8,11-tetraazabicyclo[6.6.2]hexadecane
et-cyclam: 1,4-ethano-1,4,8,11-tetraazacyclotetradecane
cylamdione: 3,9-dioxy-1,4,8,11-tetraazacyclotetradecane
diamsar: 1,8-diamino-3,6,10,13,16,19-hexaazabicyclo(6,6,6)eicosane
Polyaminocarboxylic Macrocycles
dota: 1,4,7,10-tetraazacyclododecane-1,4,7,10-tetraacetic acid
trita: 1,4,7,10-tetraazacyclotridecane-1,4,7,10-tetraacetic acid
teta: triethylenetetramine bridged-cyclam-2a: 1,4,8,11-tetraazabicyclo[6.6.2]hexadecane-1,8-di(methanephosphonic acid)
do3a: 1,4,7-tris(carboxymethyl)-1,4,7,10-tetraazacyclododecane
do2a: 1,4,7,10-tetraazacyclododecane-1,7-bis(acetic acid)
Polyaminophosphonate Macrocycles
dotp: 1,4,7,10-tetraazacyclododecane-1,4,7,10-tetra(methanephosphonic acid)
do3p: 1,4,7,10-tetraazacyclododecane-1,4,7-tri(methanephosphonic acid)
do2p: 1,4,7,10-tetraazacyclododecane-1,7-di(methanephosphonic acid)

The term "patient" or "subject" is used throughout the specification to describe an animal, preferably a human, to whom diagnosis, treatment, including prophylactic treatment, or monitoring of treatment with the compounds according to the present invention is provided. For treatment of those infections, conditions or disease states which are specific for a specific animal such as a human patient, the term patient refers to that specific animal.

The term "compound" is used herein to refer to any specific chemical compound disclosed herein. Within its use in context, the term generally refers to a single compound but in certain instances may also refer to stereoisomers and/or optical isomers (including racemic mixtures) of disclosed compounds, including pharmaceutically acceptable salts, solvates and polymorphs thereof.

The term "optionally substituted" shall mean a substituent other than H on a molecule of a compound, the substituent being compatible with the chemistry of the present invention. Substituents include $C_1$-$C_6$ alkyl groups (preferably, $C_1$-$C_3$ alkyl groups, which may be optionally substituted with for example, one or more halogen group, especially fluorine), halogen (F, Cl, Br or I), amine groups (which may be optionally substituted with one or two $C_1$-$C_3$ alkyl groups), O($C_1$-$C_6$)alkyl (alkoxy), OC(O)($C_1$-$C_6$)alkyl (ester), (O)CO($C_1$-$C_6$)alkyl (ester), $C_1$-$C_6$ amide or $C_1$-$C_6$ carboxamide (where the amine is unsubstituted, or mono- or di-$C_1$-$C_3$ alkyl substituted), among others.

The term "effective amount" is used throughout the specification to describe concentrations or amounts of compounds according to the present invention which may be used to diagnose a disease state or prognosis of a disease state, produce a favorable change in a disease or condition treated, whether that change is a remission, a favorable physiological result, a reversal or attenuation of a disease state or condition treated, the diagnosis, prevention or the reduction in the likelihood of a condition or disease-state occurring, depending upon the disease or condition treated. Where compounds are used in combination, each of the compounds is used in an effective amount, wherein an effective amount may include a synergistic amount.

The term "ICAM-1/LFA-1 mediated disease" is used throughout the specification to describe a disease which is mediated through, occurs as a consequence of the interaction of ICAM-1 with LFA-1, for example, by inhibiting the ICAM-1/LFA-1 dependent homotypic aggregation of human lymphocytes and human lymphocyte adherence to ICAM-1, or modulating immune cell activation/proliferation, for example, as competitive inhibitors of intercellular ligand/receptor binding reactions involving CAMS and leukointegrins. These disease states include numerous cancers and microbial disease states or conditions, as otherwise described herein. These disease states or conditions often produce levels of LFA-1 or ICAM receptors which are elevated as a consequence of said infectious disease state or condition and provide a target or approach for diagnosing, monitoring the treatment of and/or treating these diseases.

The present compounds and compositions may be used to treat varied diseases and conditions such as an inflammatory or immune cell-mediated diseases including arthritis, rheumatoid arthritis, osteoarthritis, diseases or conditions resulting from non-specific immune responses such as adult respiratory distress syndrome, shock, oxygen toxicity, septic shock, multiple organ injury syndrome secondary to septicemia, multiple organ injury syndrome secondary to trauma, ischemia-reperfusion injury, reperfusion injury of tissue due to cardiopulmonary bypass, myocardial infarction or use with thrombolysis agents to liquidize or eliminate thrombus, acute glomerulonephritis, vasculitis, reactive arthritis, dermatosis with acute inflammatory components, stroke, thermal injury, hemodialysis, leukapheresis, ulcerative colitis, necrotizing enterocolitis and granulocyte transfusion associated syndrome, solid organ transplant rejection, autoimmune diseases including Raynaud's syndrome, autoimmune thyroiditis, dermatitis, multiple sclerosis, arthritis, including rheumatoid arthritis and osteoarthritis, insulin-dependent diabetes mellitus, diabetes retinopathy, uveitis, inflammatory bowel disease including Crohn's disease and ulcerative colitis, and systemic lupus erythematosus, hyperproliferative diseases such as psoriasis, hyperkeratosis, ichthyosis, keratoderma, lichen planus or warts, hematopoietic neoplasms and metastasis of such neoplasms, including Hodgkin's disease, non-Hodgkin's lymphoma, leukemias, including non-acute and acute leukemias, such as acute myelogenous leukemia, acute lymphocytic leukemia, acute promyelocytic leukemia (APL), acute T-cell lymphoblastic leukemia, adult T-cell leukemia, basophilic leukemia, eosinophilic leukemia, granulocytic leukemia, hairy cell leukemia, leukopenic leukemia, lymphatic leukemia, lymphoblastic leukemia, lymphocytic leukemia, megakaryocytic leukemia, micromyeloblastic leukemia, monocytic leukemia, neutrophilic leukemia and stem cell leukemia; and in adjunct therapy in reducing the likelihood of retinoic acid syndrome in an acute promyelocytic leukemia (APL) patient being treated with retinoic acid. The compounds according to the present invention may also be used to fluidize or dissolve a thrombus in a patient, preferably in combination with a thrombolysis agent. Compounds according to the present invention may also be used to diagnose, monitor and/or treat microbial and parasitic diseases and/or conditions as otherwise disclosed herein.

In certain preferred aspects of the invention, compounds according to the present invention, and in particular, a compound according to the chemical structure;

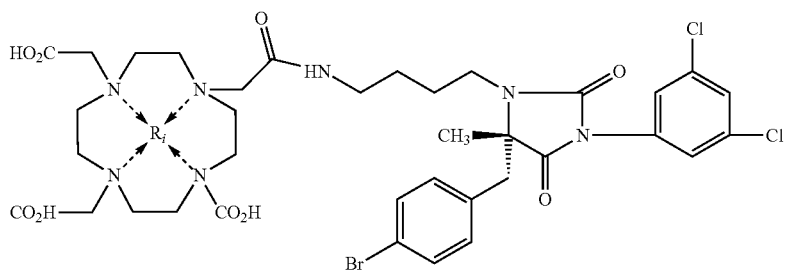

Where $R_i$ is a radioisotope (as a cation) as otherwise described hereinbelow, more preferably $^{213}$Bi, (for example, as $^{213}$Bi$^{3+}$), $^{177}$Lu (for example, as $^{177}$Lu$^{3+}$), $^{68}$Ga or $^{111}$In (for example, as $^{68}$Ga3+ or $^{111}$In3+). In particularly preferred aspects, $R_i$ are $^{68}$Ga or $^{111}$In according to the following chemical structures:

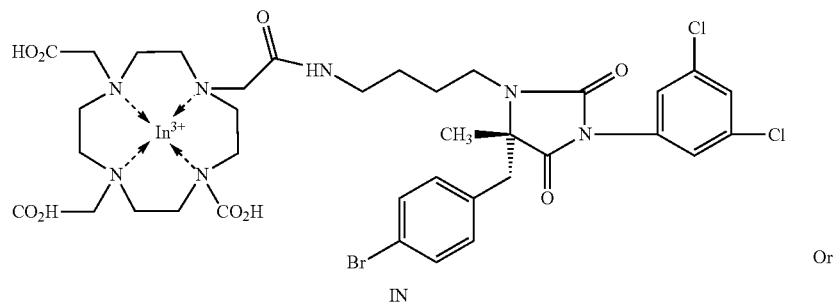

IN

Or

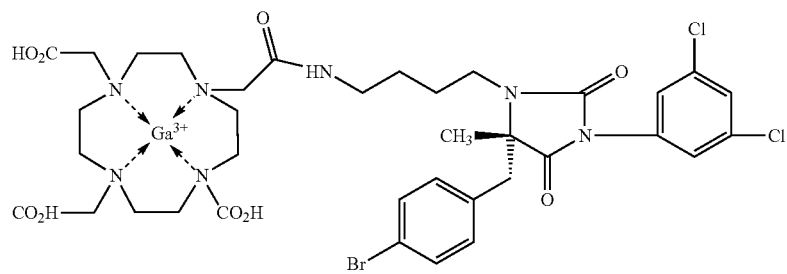

or a pharmaceutically acceptable salt, enantiomer, solvate or polymorph thereof, may be used to diagnose or treat a disease or condition in a tissue of a patient wherein the disease state or condition is caused by a microbial (bacterial, viral, protozoal, fungal) or multicellular (parasitic) infection (helminthic, other endoparasites).

The term "infectious disease" is used throughout the specification to describe clinically evident disease resulting from the presence of pathogenic microbial agents, including pathogenic viruses, pathogenic bacteria, fungi, protozoa, multicellular parasites, and aberrant proteins known as prions. These pathogens are able to cause disease in animals and/or plants. Infectious pathologies are usually qualified as contagious diseases (also called communicable diseases) due to their potentiality of transmission from one person or species to another. Transmission of an infectious disease may occur through one or more of diverse pathways including physical contact with infected individuals. These infecting agents may also be transmitted through liquids, food, body fluids, contaminated objects, airborne inhalation, or through vector-borne spread.

In the present method, the following infections or disease states, generally microbial and/or parasitic infections, may be diagnosed and/or treated (including monitoring or assisting the treatment of a disease state or condition) using one or more compounds according to the present invention:

1. Skin and soft tissue infections such as: folliculitis, furuncles, and carbuncles; erysipelas; lymphangitis; cellulitis, necrotizing soft tissue infections, diabetic foot infections, decubitus ulcers
2. Bone and joint infections such as: osteomyelitis, infectious arthritis, mastoiditis
3. Central nervous system infections arising from meningococcal, pneumococcal, diplococcal, *H. influenzae*, as well as other gram-negative and gram-positive bacterium, mycobacterium tuburculosis, *Cryptococcal neoformans*, or viral encephalitis
4. Upper and lower respiratory tract infections such as: bronchitis, bronchiolitis, pneumonia, otitis media, pharyngitis, sinusitis, epiglottitis and laryngitis
5. Infective endocarditis
6. Tuberculosis
7. Gastrointestinal infections such as: enterotoxigenic, enterhemorrhagic, and travelers diarrhea; pseudomembranous colitis; Shigelloisis; Salmonellosis; Campylobacteriosis; Yersiniosis; gasteroenteritis
8. Intra-abdominal infections of the stomach, biliary tract, proximal small-bowel, distal ileum, and colon; primary and secondary bacterial peritonitis; abscess; appendicitis; cholysystitis, cholangitis, contamination from abdominal trauma, pelvic inflammatory disease
9. Parasitic diseases, including protozoan infections, diseases from roundworms and flatworms (helminthiasis) and ectoparasites (pediculosis, acariasis), among others
10. Urinary tract infections, prostatitis, urethritis, epididymitis, cervicitis or vulvovaginitis, proctitis, salpingitis
11. Sepsis and septic shock
12. Superficial and invasive fungal infections such as: histoplasmosis, blastomycosis, coccidioidomycosis, cryptococcosis, Candidiasis, Apergillosis
13. Post-surgical infections
14. Fever of unknown origin
15. Cardiovascular diseases such as cardiovascular ischemia, coronary atherosclerosis, angina, and heart failure
16. Degenerative joint diseases including osteoarthritis (degenerative join disease) as a result of trauma to the joint, infection of the joint, or age; rheumatoid arthritis and psoriatic arthritis and/or autoimmune diseases in which the body attacks itself. Septic arthritis caused by joint infection. Gouty arthritis caused by deposition of uric acid crystals in the joint, causing inflammation
17. Bursitis inflammation of one or more bursae (small sacs) of synovial fluid in the body.
18. Diseases resultant from vascular disease or injury from atherosclerosis, ischemia, or infarct including: stroke, cerebrovascular ischemia, cerebrovascular infarct, cerebrovascular accidents, myocardial ischemia and infarct
19. Gastrointestinal inflammatory conditions such as peptic and duodenal ulcer disease, inflammatory bowel and Crohn's disease, toxic megacolon, colangeous colitis, lymphocytic colitis, ischemic colitis, diversion colitis, Behcet's colitis, inflammatory colitis The term "neoplasia" or "neoplasm" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and may invade surrounding tissues. As used herein, the term neoplasia/neoplasm is used to describe all cancerous disease states and embraces or encompasses the pathological process associated with cancer, in particular hematopoietic neoplasm and its metastasis. A hematopoietic neoplasm is a neoplasm of hematopoeitic cells of the blood or lymph system and includes disease states such as Hodgkin's disease, non-Hodgkin's lymphoma, leukemias, including non-acute and acute leukemias, such as acute myelogenous leukemia, acute lymphocytic leukemia, acute promyelocytic leukemia (APL), adult T-cell leukemia, basophilic leukemia, eosinophilic leukemia, granulocytic leukemia, hairy cell leukemia, leukopenic leukemia, lymphatic leukemia, lymphoblastic leukemia, lymphocytic leukemia, megakaryocytic leukemia, micromyeloblastic leukemia, monocytic leukemia, neutrophilic leukemia and stem cell leukemia.

The term "prophylactic" is used to describe the use of a compound described herein which either prevents or reduces the likelihood of a condition or disease state in a patient or subject.

The term "pharmaceutically acceptable" refers to a salt form of the present compounds (an acid or base addition salt, among others well known in the art) or a carrier, additive or excipient which is not unacceptably toxic to the subject to which it is administered. Compounds according to the present invention include pharmaceutically acceptable salt forms where applicable.

The term "imaging" or "nuclear imaging" is used to describe standard well-known nuclear imaging techniques, including especially radiation (radionuclide) imaging, including scintigraphic imaging, which compares radiation emitted from a tissue to be diagnosed, monitored or treated, in comparison to a normal standard, which provides a means by which the condition of a tissue may be diagnosed or monitored. In diagnosis, radioactive substances according to the present invention are administered to a patient and the radiation emitted is detected. The diagnostic tests involve the formation of an image using a gamma camera or positron emission tomography, sometimes called an Anger gamma camera. Imaging may also be referred to as radionuclide imaging or nuclear scintigraphy. The images which are created from tissue to be diagnosed are than compared to a standard which is created from a representative normal tissue sample. Tissue which is diseased and the extent of disease may be diagnosed accordingly. In the case of monitoring a disease state pursuant to a treatment modity or therapy, disease tissue at a point in time is compared to normal tissue as well as diseased tissue at an earlier point in time when therapy had not yet been initiated or was early in the treatment phase. In the present invention, in certain methods, single photon emission computed tomography (SPECT) may be used. SPECT is a nuclear medicine tomographic imaging technique which uses gamma rays. It is very similar to conventional nuclear medicine planar imaging using a gamma camera. The present compounds, compositions and methods are readily adaptable to conventional nuclear medicine techniques to provide diagnositic, monitoring and therapeutic approaches pursuant to the present invention.

The term "standard" is used to describe a set or reference measurement(s) made with for example, normal or non-diseased tissue (or, in some cases diseased and non-treated tissue) such that a comparison with a tested sample or samples can be made to determine the existence or absence of a disease-state or condition in the tested sample (which is usually in the patient's body) or the effectiveness of a therapeutic treatment. In the present invention, standards may be determined by taking measurements using normal tissue and/or the absence of a condition or disease state or a measurement, among other methods, for which the diagnostic assay is used. Standards are well known in the art and are determined using well known methods available in the art. Standards may vary from application to application depending upon the diagnostic method utilized.

The term "tumor" is used to describe a malignant or benign growth or tumefacent.

The term "anti-cancer compound" or "anti-cancer agent" is used to describe any compound (including its derivatives) other than the present compounds as otherwise described herein which may be used to treat cancer. Anti-cancer agents as described hereunder are a subset of cytotoxic agents which may be used in the present invention. Exemplary anti-cancer compounds for use in the present invention include antimetabolite agents which are broadly characterized as antimetabolites, inhibitors of topoisomerase I and II, alkylating agents and microtubule inhibitors (e.g., taxol), as well as tyrosine kinase inhibitors (e.g., surafenib), EGF kinase inhibitors (e.g., tarceva or erlotinib) and ABL kinase inhibitors (e.g. gleevec or imatinib). Anti-cancer compounds for use in the present invention include, for example, Aldesleukin; Alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfan oral; calusterone; capecitabine; carboplatin; carmustine; carmustine with Polifeprosan 20 Implant; celecoxib; chlorambucil; cisplatin; cladribine; cyclophosphamide; cytarabine; cytarabine liposomal; dacarbazine; dactinomycin; actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemtuzumab ozogamicin; gleevec (imatinib); goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); meclorethamine (nitrogen mustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; oxaliplatin; paclitaxel; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; surafenib; talbuvidine (LDT); talc; tamoxifen; tarceva (erlotinib); temozolomide; teniposide (VM-26); testolactone; thioguanine (6-TG); thiotepa; topotecan; toremifene; Tositumomab; Trastuzumab; tretinoin (ATRA); Uracil Mustard; valrubicin; valtorcitabine (monoval LDC); vinblastine; vinorelbine; zoledronate; and mixtures thereof, among others.

The term "antimicrobial agent" is used to describe a therapeutic compound or bioactive agent which may be used to treat a microbial infection, i.e., an infection caused by a bacteria, virus, protozoa or fungus. The antimicrobial agent may be an antibiotic, an antifungal agent, an antiviral or an antiprotozoal or antiparasitic agent (which may also be used to treat multicellular parasites). These agents may be coadministered alone in combination with a radionuclide compound according to the present invention in order to treat an infection in a patient.

The term "antibiotic" is used to describe a chemotherapeutic agent which is active against bacteria. In common usage, an antibiotic is a substance or compound (also called chemotherapeutic agent) that kills or inhibits the growth of bacteria. Antibiotics belong to the group of antimicrobial compounds used to treat infections caused by micro-organisms, including fungi and protozoa. The term "antibiotic" was coined in the 1940's to describe any substance produced by a micro-organism that is antagonistic to the growth of other micro-organisms in high dilution. This original definition excluded naturally occurring substances, such as gastric juice and hydrogen peroxide (they kill bacteria but are not produced by micro-organisms), and also excluded synthetic compounds such as the sulfonamides (which are antimicrobial agents). Many antibiotics are relatively small molecules with a molecular weight less than 2000 Da. With advances in medicinal chemistry, most antibiotics are now modified chemically from original compounds found in nature, as is the case with beta-lactams (which include the penicillins, produced by fungi in the genus *Penicillium*, the cephalosporins, and the carbapenems). Some antibiotics are still produced and isolated from living organisms, such as the aminoglycosides; in addition, many more have been created through purely synthetic means, such as the quinolones.

Unlike many previous treatments for infections, which often consisted of administering chemical compounds such as strychnine and arsenic, with high toxicity also against mammals, most antibiotics from microbes have fewer side-effects, and high effective target activity. Most anti-bacterial antibiotics do not have activity against viruses, fungi, or other microbes. Anti-bacterial antibiotics can be categorized based on their target specificity: "narrow-spectrum" antibiotics target particular types of bacteria, such as Gram-negative or Gram-positive bacteria, while broad-spectrum antibiotics affect a wide range of bacteria. Antibiotics which target the bacterial cell wall (penicillins, cephalosporins, cephems), or cell membrane (polymixins), or interfere with essential bacterial enzymes (quinolones, sulfonamides) usually are bactericidal in nature. Those which target protein synthesis such as the aminoglycosides, macrolides and tetracyclines are usually bacteriostatic. In the last few years three new classes of antibiotics have been brought into clinical use. These new antibiotics are of the following three classes: cyclic lipopeptides (daptomycin), glycylcyclines (tigecycline), and oxazolidinones (linezolid). Tigecycline is a broad-spectrum antibiotic, while the two others are used for Gram-positive infections.

The term "antiviral agent" is used to describe a chemical agent which is used to treat a virus infection. Numerous antiviral agents may be used in the present invention. Antiviral drugs are a class of medication used specifically for treating viral infections. Like antibiotics for bacteria, specific antivirals are used for specific viruses. Unlike antibiotics, however, antiviral drugs do not destroy their target pathogen, they only inhibit their development. Antiviral drugs are one class of antimicrobials, a larger group which also includes antibiotic, antifungal and antiparasitic drugs. They are relatively harmless to the host, and therefore can be used to treat infections. They should be distinguished from viricides, which actively destroy virus particles outside the body.
Most of the antivirals now available are designed to help deal with HIV, herpes viruses (causing cold sores and genital herpes, amongst a wide range of diseases), the hepatitis B and C viruses, which can cause hepatitis and liver cancer, and influenza A and B viruses. Researchers are now working to extend the range of antivirals to other families of pathogens.

The term "antifungal agent" is used to describe a therapeutic compound or bioactive agent which may be used to treat a fungal infection in a patient. An antifungal drug is a medication used to treat fungal infections such as athlete's foot, ringworm, candidiasis (thrush), serious systemic infections such as cryptococcal meningitis, and related fungal infections. Antifungal agents for use in the present invention include, for example, polyene antifungals, imidazole, triazole and thiazole antifungals, allylamines, echinocandins, griseofulvin, flycystosine, undecylenic acid, among others.

The term "antiparasitic agent" is used to describe a therapeutic compound or bioactive agent that is used to treat parasitic diseases including nematodes, cestodes, trematodes, infectious protozoa, and amoebas. Antiparasitic agents for use in the present invention include antinematodes (mebendazole, pyrantel pamoate, thiabendazole, diethycarbazine), anticestodes (niclosamide, praziquantel), antitrematodes (praziquantel), antiamoebics (rifampin and amphotericin B), antiprotozoals (melarsoprol, eflornithine, metronidazole and timidazole), among others. These are used to treat infections and/or disease states including roundworm infections, tapeworm infections, lymphatic filariasis, and fungal sleeping sickness (Trypanosoma, including for Trypanasoma brucei), among others.

The term "antihelminthic agent" is used to describe a therapeutic compound or bioactive agent which may be used to treat a multicellular parasitic infection. It is a subset of antiparasitic agents, otherwise described herein.

The term "coadministration" or "combination therapy" is used to describe a therapy in which at least two active compounds (one of which is a compound according to the present invention) in effective amounts are used to treat cancer or another disease state or condition as otherwise described herein at the same time. Although the term coadministration preferably includes the administration of two active compounds to the patient at the same time, it is not necessary that the compounds be administered to the patient at the same time, although effective amounts of the individual compounds will be present in the patient at the same time. Compounds according to the present invention may be administered with one or more antibiotic, antifungal agent, antiviral agent or antiprotozoal or antiparasitic agent (which may also be used to treat multicellular parasites) as described hereinabove, or an anti-cancer agent, including antimetabolites, alkylating agents, topoisomerase I and topoisomerase II inhibitors as well as microtubule inhibitors, among others.

Anticancer compounds for use in the present invention include those described above, and mixtures thereof, among others. Coadministration of one of the present compounds with another anticancer agent as otherwise described herein will often result in a synergistic enhancement of the anticancer activity of the other anticancer agent, an unexpected result.

One or more of the present compounds may also be coadministered with another bioactive agent (e.g., an antimicrobial agent such as an antibiotic, antiviral agent, antifungal agent or antiprotozoal agent or an antihelminthic agent or other antiparasitic agent) which treats an infectious disease to be diagnosed, monitored or treated hereunder. Thus, pharmaceutical compositions according to the present invention may also include an effective amount of one or more antimicrobial agents in combination with the radionuclide containing compound. Antimicrobial agents include, for example, antibiotics, which are effective against gram-positive and gram-negative bacteria, anti-fungal agents, anti-parasitic agents and anti-viral agents, among numerous others, as described hereinabove. More specifically, these compounds include, for example, antibiotics, such as penicillins, cephalosporins, cephams (including carbacephams and cephamycins), polymixins, quinolones, sulfonamides, aminoglycosides, macrolides, tetracyclines, cyclic lipopeptides (e.g., daptomycin), glycylcyclines (eg., tigecycline), and oxazolidinones (linezolid), antiviral agents, especially including anti-hepatitis B and anti-hepatitis C viral agents, antifungal agents, including polyene antifungals, imidazole, triazole and thiazole antifungals, allylamines, echinocandins and specific antifungals such as griseofulvin, flycystosine, and undecylenic acid, among others, and antiparasitic agents such as antinematodes (mebendazole, pyrantel pamoate, thiabendazole, diethycarbazine), anticestodes (niclosamide, praziquantel), antitrematodes (praziquantel), antiamoebics (rifampin and amphotericin B), and antiprotozoals (melarsoprol, eflornithine, metronidazole and timidazole). Specific antibiotics for use in the include, for example, amoxycillin, ampicillin, penicillin, levofloxacin, gatifloxacin, moxifloxacin, ciprofloxacin, co-amoxiclav; streptomycin, oxytetracycline, tetracycline, doxycycline and chloramphenical, among numerous others.

In certain aspects, a diagnostic agent as described herein may be combined with an antimicrobial agent as otherwise described herein to allow a combined therapeutic monitoring and therapeutic method to be provided in a single pharmaceutical agent. Pharmaceutical compositions comprising at least one diagnostic compound in combination with a therapeutic compound, especially an antiobiotic, antiviral agent, antifungal agent or anti-parasitic agent as otherwise disclosed herein in effective amounts, in combination with a pharmaceutically acceptable, carrier, additive or excipient represent additional aspects of the present invention. In this aspect of the invention, a single pharmaceutical composition may be used to administer at least one therapeutic agent in combination with one or more diagnostic compound as disclosed herein, which may be used to monitor the impact of the therpeutic compound on the infection treated with the therapeutic agent.

The present invention also relates to a diagnostic aspect of the invention which comprises administering a compound according to the present invention to a patient or subject to determine the existence of a disease or condition where LFA-1 expression is elevated such as in cancer, especially a leukemia or lymphoma, an inflammatory disease or an infectious disease as otherwise described herein and through measuring the radioactive decay of the isotope through any method known in the art, as discussed above, determining the presence of disease and state of the tissue in the patient or subject. The diagnostic method according to the present invention may facilitate therapy once diagnosis of cancer or other disease state or condition, especially including the infectious disease as otherwise described herein is made.

In preferred aspects of the invention, a compound according to the chemical structure:

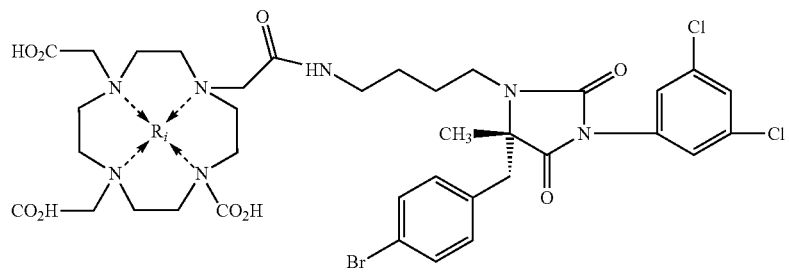

Where Rn is a radioisotope as otherwise described hereinbelow, more preferably $^{213}$Bi, $^{177}$Lu, $^{201}$Tl or $^{111}$In or a pharmaceutically acceptable salt thereof is administered to a patient to diagnose the existence of disease state or condition in a patient. In particularly preferred aspects, Rn are $^{68}$Ga $^{111}$In according to the following chemical structure:

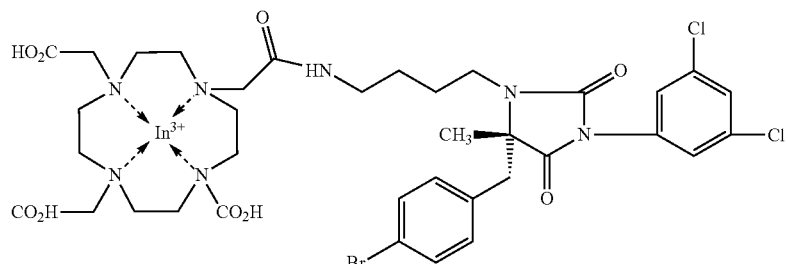

IN

Or

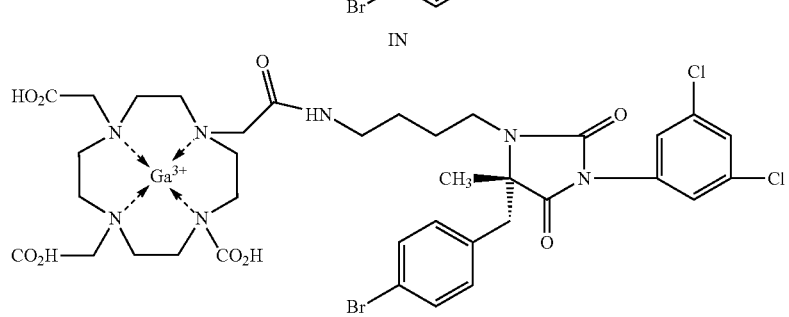

These compounds are shown to have superior bioavailability in numerous tissues, such that concentrations of compound may be used to diagnose the existence of disease states or conditions as otherwise disclosed herein.

In an additional aspect of the present invention, the present compounds and compositions may be used to monitor and/or treat infectious diseases and conditions which are mediated through a cellular response which is undesirable and/or which should be controlled or inhibited, especially including where LFA-1 expression is elevated. Such infectious disease states or conditions may include bacterial infections, viral infections, fungal infections and parasitic infections, as well as other infections as disclosed in greater detail hereinabove.

With respect to infectious diseases, the compounds and compositions according to the present invention may be used to diagnose, monitor and/or treat bacterial, viral, fungal and/or parasitic infections related to the following:

1. Skin and soft tissue infections such as: folliculitis, furuncles, and carbuncles; erysipelas; lymphangitis; cellulitis, necrotizing soft tissue infections, diabetic foot infections, decubitus ulcers 2. Bone and joint infections such as: osteomyelitis, infectious arthritis, mastoiditis 3. Central nervous system infections arising from meningococcal, pneumococcal, diplococcal, *H. influenzae*, as well as other gram-negative and gram-positive bacterium, mycobacterium tuberculosis, *Cryptococcal neoformans*, or viral encephalitis 4. Upper and lower respiratory tract infections such as: bronchitis, bronchiolitis, pneumonia, otitis media, pharyngitis, sinusitis, epiglottitis and laryngitis 5. Infective endocarditis 6. Tuberculosis 7. Gastrointestinal infections such as: enterotoxigenic, enterohemorrhagic, and travelers diarrhea; pseudomembranous colitis; Shigelloisis; Salmonellosis; Campylobacteriosis; Yersiniosis; gasteroenteritis 8. Intra-abdominal infections of the stomach, biliary tract, proximal small-bowel, distal ileum, and colon; primary and secondary bacterial peritonitis; abscess; appendicitis; cholysystitis, cholangitis, contamination from abdominal trauma, pelvic inflammatory disease 9. Parasitic diseases, including protozoan infections, diseases from roundworms and flatworms (helminthiasis) and ectoparasites (pediculosis, acariasis), among others 10. Urinary tract infections, prostatitis, urethritis, epididymitis, cervicitis or vulvovaginitis, proctitis, salpingitis 11. Sepsis and septic shock 12. Superficial and invasive fungal infections such as: histoplasmosis, blastomycosis, coccidioidomycosis, cryptococcosis, Candidiasis, Apergillosis 13. Post-surgical infections 14. Fever of unknown origin 15. Cardiovascular diseases such as cardiovascular ischemia, coronary atherosclerosis, angina, and heart failure 16. Degenerative joint diseases including osteoarthritis (degenerative joint disease) as a result of trauma to the joint, infection of the joint, or age; rheumatoid arthritis and psoriatic arthritis and/or autoimmune diseases in which the body attacks itself. Septic arthritis caused by joint infection. Gouty arthritis caused by deposition of uric acid crystals in the joint, causing inflammation 17. Bursitis inflammation of one or more bursae (small sacs) of synovial fluid in the body.

18. Diseases resultant from vascular disease or injury from atherosclerosis, ischemia, or infarct including: stroke, cerebrovascular ischemia, cerebrovascular infarct, cerebrovascular accidents, myocardial ischemia and infarct 19. Gasterointestinal inflammatory conditions such as peptic and duodenal ulcer disease, inflammatory bowel and Crohn's disease, toxic megacolon, colangeous colitis, lymphocytic colitis, ischemic colitis, diversion colitis, Behcet's colitis, inflammatory colitis Without being limited by way of theory, it is believed that the present compounds may be used therapeutically either by virtue of the inhibitory or stimulatory activity of the compounds within the context of the therapy of the disease state or condition.

The present invention is also directed to pharmaceutical compositions comprising an effective amount of a compound according to the present invention, including the pharmaceutically acceptable acid or base addition salts of compounds of the present invention, optionally in combination with a pharmaceutically acceptable carrier, additive or excipient. These compounds may be used alone or in combination with other bioactive agents, including antibiotics, antiviral agents, antifungal agents and antiparasitic agents, among others, which are useful for treating or monitoring the treatment of and treating any one or more of the disease states, including infectious disease states and/or conditions which are described herein.

While not being limited by way of theory, it is believed that the novel molecules of the present invention inhibit or otherwise modulate the ICAM-1/LFA-1 dependent homotypic aggregation of human lymphocytes and human lymphocyte adherence to ICAM-1. While not being limited by way of theory, it is believe that these compounds have therapeutic utility in the modulation of immune cell activation/proliferation, e.g., as competitive inhibitors or stimulators (because of the introduction of radiation) of intercellular ligand/receptor binding reactions involving CAMs and Leukointegrins. Thus the activity and therapeutic activity of compounds according to the present invention is broad-based.

Regardless of the mechanism, the compounds of the present invention may be used to diagnose, identify, monitor and/or treat conditions or disease states in patients or subjects who suffer from those conditions or disease states or are at risk for disease states or conditions from microbial and/or parasitic infections including:

1. Skin and soft tissue infections such as: folliculitis, furuncles, and carbuncles; erysipelas; lymphangitis; cellulitis, necrotizing soft tissue infections, diabetic foot infections, decubitus ulcers 2. Bone and joint infections such as: osteomyelitis, infectious arthritis, mastoiditis 3. Central nervous system infections arising from meningococcal, pneumococcal, diplococcal, *H. influenzae*, as well as other gram-negative and gram-positive bacterium, mycobacterium tuburculosis, *Cryptococcal neoformans*, or viral encephalitis 4. Upper and lower respiratory tract infections such as: bronchitis, bronchiolitis, pneumonia, otitis media, pharyngitis, sinusitis, epiglottitis and laryngitis 5. Infective endocarditis 6. Tuberculosis 7. Gastrointestinal infections such as: enterotoxigenic, enterhemorrhagic, and travelers diarrhea; pseudomembranous colitis; Shigelloisis; Salmonellosis; Campylobacteriosis; Yersiniosis; gasteroenteritis 8. Intra-abdominal infections of the stomach, biliary tract, proximal small-bowel, distal ileum, and colon; primary and secondary bacterial peritonitis; abscess; appendicitis; cholysystitis, cholangitis, contamination from abdominal trauma, pelvic inflammatory disease 9. Parasitic diseases, including protozoan infections, diseases from roundworms and flatworms (helminthiasis) and ectoparasites (pediculosis, acariasis), among others 10. Urinary tract infections, prostatitis, urethritis, epididymitis, cervicitis or vulvovaginitis, proctitis, salpingitis 11. Sepsis and septic shock 12. Superficial and invasive fungal infections such as: histoplasmosis, blastomycosis, coccidioidomycosis, cryptococcosis, Candidiasis, Apergillosis 13. Post-surgical infections 14. Fever of unknown origin.

15. Cardiovascular diseases such as cardiovascular ischemia, coronary atherosclerosis, angina, and heart failure 16. Degenerative joint diseases including osteoarthritis (degenerative joint disease) as a result of trauma to the joint, infection of the joint, or age; rheumatoid arthritis and psoriatic arthritis and/or autoimmune diseases in which the body attacks itself. Septic arthritis caused by joint infection. Gouty arthritis caused by deposition of uric acid crystals in the joint, causing inflammation 17. Bursitis inflammation of one or more bursae (small sacs) of synovial fluid in the body.

18. Diseases resultant from vascular disease or injury from atherosclerosis, ischemia, or infarct including: stroke, cerebrovascular ischemia, cerebrovascular infarct, cerebrovascular accidents, myocardial ischemia and infarct 19. Gasterointestinal inflammatory conditions such as peptic and duodenal ulcer disease, inflammatory bowel and Crohn's disease, toxic megacolon, colangeous colitis, lymphocytic colitis, ischemic colitis, diversion colitis, Behcet's colitis, inflammatory colitis The compounds of the present invention may also be used to treat varied diseases and conditions such as an inflammatory or immune cell-mediated diseases including arthritis, rheumatoid arthritis, osteoarthritis, diseases or conditions resulting from non-specific immune responses such as adult respiratory distress syndrome, shock, oxygen toxicity, septic shock, multiple organ injury syndrome secondary to septicemia, multiple organ injury syndrome secondary to trauma, ischemia-reperfusion injury, reperfusion injury of tissue due to cardiopulmonary bypass, myocardial infarction or use with thrombolysis agents to liquidize or eliminate thrombus, acute glomerulonephritis, vasculitis, reactive arthritis, dermatosis with acute inflammatory components, stroke, thermal injury, hemodialysis, leukapheresis, ulcerative colitis, necrotizing enterocolitis and granulocyte transfusion associated syndrome, solid organ transplant rejection, autoimmune diseases including Raynaud's syndrome, autoimmune thyroiditis, dermatitis, multiple sclerosis, arthritis, including rheumatoid arthritis and osteoarthritis, insulin-dependent diabetes mellitus, diabetes retinopathy, uveitis, inflammatory bowel disease including Crohn's disease and ulcerative colitis, and systemic lupus erythematosus, hyperproliferative diseases such as psoriasis, hyperkeratosis, ichthyosis, keratoderma, lichen planus or warts, hematopoietic neoplasms and metastasis of such neoplasms, including Hodgkin's disease, non-Hodgkin's lymphoma, leukemias, including non-acute and acute leukemias, such as acute myelogenous leukemia, acute lymphocytic leukemia, acute promyelocytic leukemia (APL), acute T-cell lymphoblastic leukemia, adult T-cell leukemia, basophilic leukemia, eosinophilic leukemia, granulocytic leukemia, hairy cell leukemia, leukopenic leukemia, lymphatic leukemia, lymphoblastic leukemia, lymphocytic leukemia, megakaryocytic leukemia, micromyeloblastic leukemia, monocytic leukemia, neutrophilic leukemia and stem cell leukemia; and in adjunct therapy in reducing the likelihood of retinoic acid syndrome in an acute promyelocytic leukemia (APL) patient being treated with retinoic acid. The compounds according to the present invention may also be used to fluidize or dissolve a thrombus in a patient, preferably in combination with a thrombolysis agent.

Thus, another aspect of the invention is the provision of a method for the treatment or prophylaxis of the above-described conditions in a patient in need thereof through the administration of therapeutic or prophylactic effective amounts of one or more compounds of the present invention.

In accordance with the method provided by the invention, the novel compounds of formula I in effective amounts may be administered to a patient for a diagnostic, prophylactic or therapeutic purpose, including monitoring of therapy, either alone or with other agents, including other immunosuppressive or antiinflammatory agents or other anti-cancer agents and especially antimicrobial agents, such as antibiotics, antiviral agents, antifungal agents and antiprotozoal agents, as well as antihelminthic and other antiparasatic agents. When provided prophylactically, the immunosuppressive compound(s) are provided in advance of any inflammatory response or symptom (for example, prior to, at, or shortly after the time of an organ or tissue transplant but in advance of any symptoms of organ rejection). The prophylactic administration of a compound of the formula I serves to prevent or attenuate any subsequent inflammatory response (such as, for example, rejection of a transplanted organ or tissue, etc.). The therapeutic administration of a compound of the formula I serves to attenuate any actual inflammation (such as, for example, the rejection of a transplanted organ or tissue). Thus, in accordance with the invention, a compound of the formula I can be administered either prior to the onset of inflammation (so as to suppress an anticipated inflammation) or after the initiation of inflammation.

The novel compounds of formula I may, in accordance with the invention, be administered in single or divided doses by the oral, parenteral or topical routes. Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Administration of compounds according to the present invention as sprays, mists, or aerosols for intra-nasal, intra-tracheal or pulmonary administration may also be used. The present invention therefore also is directed to pharmaceutical compositions comprising an effective amount of a compound according to the present invention, optionally in combination with a pharmaceutically acceptable carrier, additive or excipient.

The amount used is that amount effective within the context of the administration. A suitable oral dosage for a compound of formula I would be in the range of about 0.01 mg to 10 g or more per day, preferably about 0.1 mg to about 1 g per day. In parenteral formulations, a suitable dosage unit may contain from 0.1 to 250 mg of said compounds, which may be administered from one to four times per day, whereas for topical administration, formulations containing 0.01 to 1% active ingredient are preferred. It should be understood, however, that the dosage administration from patient to patient will vary and the dosage for any particular patient will depend upon the clinician's judgment, who will use as criteria for fixing a proper dosage the size and condition of the patient as well as the patient's response to the drug.

When the compounds of the present invention are to be administered by the oral route, they may be administered as medicaments in the form of pharmaceutical preparations which contain them in association with a compatible pharmaceutical carrier, additive or excipient material. Such carrier material can be an inert organic or inorganic carrier material suitable for oral administration. Examples of such carrier materials are water, gelatin, talc, starch, magnesium stearate, gum arabic, vegetable oils, polyalkylene-glycols, petroleum jelly and the like.

The pharmaceutical preparations can be prepared in a conventional manner and finished dosage forms can be solid dosage forms, for example, tablets, dragees, capsules, and the like, or liquid dosage forms, for example solutions, suspensions, emulsions and the like.

The pharmaceutical preparations may be subjected to conventional pharmaceutical operations such as sterilization. Further, the pharmaceutical preparations may contain conventional adjuvants such as preservatives, stabilizers, emulsifiers, flavor-improvers, wetting agents, buffers, salts for varying the osmotic pressure and the like. Solid carrier material which can be used include, for example, starch, lactose, mannitol, methyl cellulose, microcrystalline cellulose, talc, silica, dibasic calcium phosphate, and high molecular weight polymers (such as polyethylene glycol).

For parenteral use, a compound according to the present invention can be administered in an aqueous or non-aqueous solution, suspension or emulsion in a pharmaceutically acceptable oil or a mixture of liquids, which may contain bacteriostatic agents, antioxidants, preservatives, buffers or other solutes to render the solution isotonic with the blood, thickening agents, suspending agents or other pharmaceutically acceptable additives. Additives of this type include, for example, tartrate, citrate and acetate buffers, ethanol, propylene glycol, polyethylene glycol, complex formers (such as EDTA), antioxidants (such as sodium bisulfite, sodium metabisulfite, and ascorbic acid), high molecular weight polymers (such as liquid polyethylene oxides) for viscosity regulation and polyethylene derivatives of sorbitol anhydrides.

Preservatives may also be added if necessary, such as benzoic acid, methyl or propyl paraben, benzalkonium chloride and other quaternary ammonium compounds.

The compounds of this invention may also be administered as solutions for nasal application and may contain in addition to the compounds of this invention suitable buffers, tonicity adjusters, microbial preservatives, antioxidants and viscosity-increasing agents in an aqueous vehicle. Examples of agents used to increase viscosity are polyvinyl alcohol, cellulose derivatives, polyvinylpyrrolidone, polysorbates or glycerin. Preservatives added may include benzalkonium chloride, chloro-butanol or phenylethyl alcohol, among numerous others.

Additionally, the compounds provided by the invention can be administered by suppository.

In certain aspects according to the present invention, where various cancers are to be treated, the compounds may be co-administered with at least one other anti-cancer agent such as antimetabolites, Ara C, etoposide, doxorubicin, taxol, hydroxyurea, vincristine, cytoxan (cyclophosphamide) or mitomycin C, among numerous others, including topoisomerase I and topoisomerase II inhibitors, such as adriamycin, topotecan, campothecin and irinotecan, other agents such as gemcitabine and agents based upon campothecin and cisplatin, among numerous other anti-cancer compounds including tyrosine kinase inhibitors (e.g., surafenib), EGF kinase inhibitors (e.g., tarceva or erlotinib) and ABL kinase inhibitors (e.g. gleevec or imatinib), as well as Aldesleukin; Alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfan oral; calusterone; capecitabine; carboplatin; carmustine; carmustine with Polifeprosan 20 Implant; celecoxib; chlorambucil; cisplatin; cladribine; cyclophosphamide; cytarabine; cytarabine liposomal; dacarbazine; dactinomycin; actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemtuzumab ozogamicin; gleevec (imatinib); goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); meclorethamine (nitrogen mustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; oxaliplatin; paclitaxel; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; surafenib; talbuvidine (LDT); talc; tamoxifen; tarceva (erlotinib); temozolomide; teniposide (VM-26); testolactone; thioguanine (6-TG); thiotepa; topotecan; toremifene; Tositumomab; Trastuzumab; tretinoin (ATRA); Uracil Mustard; valrubicin; valtorcitabine (monoval LDC); vinblastine; vinorelbine; zoledronate; and mixtures thereof, among others. By "co-administer" it is meant that the present compounds are administered to a patient such that the present compounds as well as the co-administered compound may be found in the patient's bloodstream at the same time, regardless when the compounds are actually administered, including simultaneously. In many instances, the co-administration of the present compounds with traditional anticancer agents produces a synergistic (i.e., more than additive) result which is unexpected.

In aspects related to monitoring and/or treating tissue with microbial infections (infectious disease), radionuclide compounds according to the present invention may be coadministered with an effective amount of antimicrobial agent (antibiotic, antiviral agent, antifungal agent or antiprotozoal agent or antiparasitic agent) in order to treat or monitor and treat the microbial infection in the tissue. Examples of these compounds include, for example antibiotics, such as penicillins, cephalosporins, cephams (including carbacephams and cephamycins), polymixins, quinolones, sulfonamides, aminoglycosides, macrolides, tetracyclines, cyclic lipopeptides (e.g., daptomycin), glycylcyclines (eg., tigecycline), and oxazolidinones (linezolid), antiviral agents, especially including anti-hepatitis B and anti-hepatitis C viral agents (nucleosides), anti-influenza agents (oseltamivir or Tamiflu), antifungal agents, including polyene antifungals, imidazole, triazole and thiazole antifungals, allylamines, echinocandins and specific antifungals such as griseofulvin, flycystosine, and undecylenic acid, among others, and antiparasitic agents such as antinematodes (mebendazole, pyrantel pamoate, thiabendazole, diethycarbazine), anticestodes (niclosamide, praziquantel), antitrematodes (praziquantel), antiamoebics (rifampin and amphotericin B), and antiprotozoals (melarsoprol, eflornithine, metronidazole and timidazole). Specific antibiotics for use in the include, for example, amoxycillin, ampicillin, penicillin, levofloxacin, gatifloxacin, moxifloxacin, ciprofloxacin, co-amoxiclav; streptomycin, oxytetracycline, tetracycline, doxycycline and chloramphenical, among numerous others.

The present invention is further exemplified by the examples which are attached. They are to be taken as purely exemplary and without limitation.

EXAMPLES

Research Methods

Radiolabelling the DOTA-alkylamino-NorBirt with radionuclide and determining its specific activity, specific binding and integrity towards LFA-1 receptors utilizing in vitro receptor studies may be performed according to the methods which are described in detail in US patent application No. 20070048216, which is incorporated by reference herein.
Objective:
To evaluate the in vivo molecular imaging potential of this compound in a pre-clinical model of infection/inflammation.
Methods:
Radiolabeling The radiometal $^{111}$In was incorporated into alkylamino-NorBIRT through 1,4,7,10-tetraazacyclododecane-N, N'N"N"'-tetraacetic acid (DOTA) as a chelator. $^{111}$In chloride (high purity) was purchased through Mallinckrodt (United States). Synthesis of the alkylamino-NorBIRT is described in detail in Cancer Biotherapy and Radiopharmaceuticals Volume 21, Number 5, 2006, pages 418-426.

DOTA-butylamino-NorBIRT was dissolved in ultrapure water. $^{111}$In-chloride was placed in a metal free tube and the NorBirt solution was added. The solution was mixed and then buffered to a pH of 5-6 using a 3M ammonium acetate buffer. The solution was heated in a hot block for 30 minutes at 100° C. The reaction mixture (50 uL) was added to 200 uL of 4 mM diethylenetriaminepentaacetic acid (DTPA, Mallinckrodt Baker Inc., Paris, Ky.).

Incorporation yield was determined using ITLC silica gel strips (Gelman Sciences, Inc., Ann Arbor, Mich.) with 0.9% NaCl USP solution (Hospira Inc., Lake Forest, Ill.). Stripes were analyzed on an AR2000 (Bioscan Inc., Washington, D.C.).

Cell Culture

E. coli. cells were obtained from a commercial source, reconstituted and incubated 24-72 hours in standard media according to the manufacturer's instructions [more specifics to follow].

Infection Model

Normal C57Blk6 male mice were inoculated intramuscularly with 1E7-9 E. coli cells in approximately 0.8 mL in the muscle overlying the left femur, the proximal hind leg.

Biodistribution

An initial biodistribution study was carried out in three (3) animals 24 hours post-inoculation of ~5E8 E. coli at 5 hours post-injection DOTA-alkylamino-NorBIRT. Results were evaluated as the percent injected dose per gram of tissue. The organs assessed were the heart, blood, stomach, liver, spleen, adrenals, kidneys, bone, muscle, bladder, testes, as well as the abcess or site of infection.

Imaging

Mice were imaged with the Bioscan NanoSPECT/CT imaging system. Dynamimc images were obtained immediately following injection of ~750 uCi of $^{111}$In-DOTA-alkylamino-NorBIRT intravenously. Static images were also obtained at 2, 4, and 24 hours post injection. Images are individually shown below.

Results:

ITLC analyses of $^{111}$In-DOTA-alkylamino-NorBIRT demonstrated ≥98% incorporation yield. The specific activity achieved was 473 Ci/mmol. SPECT/CT images with $^{111}$In-alkylaminoNorBIRT show focal uptake in the site of infection, and prompt and significant urinary excretion as soon as 5 minutes post-injection and at all subsequent time points.

Discussion:

The radiometal $^{111}$In is a polyvalent cationic metal that is an ideal candidate for SPECT imaging with 173 and 245 keV energy peaks. Gallium-68 is a similar polyvalent, cationic radiometal with chemical behavior akin to indium that undergoes radioactive decay by positron emission. Thus, it is proposed that 68Ga-alkylaminoNorBIRT would show similar desirable imaging properties useful in positron-emission tomography or PET. Our previous research has shown these and other radiometals to be effectively incorporated in many DOTA compounds.

Early images obtained 5 minutes post-injection show high concentrations of $^{111}$In-alkylaminoNorBIRT uptake/retention at the site of infection. This focal uptake persists and all observed time points, including images obtained 24 hours post-injection. There is prompt and significant radioactivity in the bladder and no focal retention in any other tissues. Biodistribution data obtained following gross dissection of mice at 18 and 24 hrs post-inoculation and tissue harvest correlate well with image-based pharmacokinetic data.

Conclusion:

These data show that $^{68}$Ga- or $^{111}$In-alkylaminoNorBIRT are highly selective imaging probes for LFA-1 receptor expression, demonstrating high sensitivity and specificity for in vivo SPECT/PET imaging sites of infection and inflammation.

LITERATURE CITED

1. Inghirami G, Wieczorek R, Zhu B. Y, et. al. Differential Expression of LFA-1 Molecules in Non-Hodgkin, s Lymphoma and Lyphoid Leukemia. *Blood.* 1988; 72:1431-1434.
2. Horst E, Radaszkiewicz T, Pals S T, et. al. Expression of the leucocyte integrin LFA-1 (CD11a/CD18) and its ligand ICAM-1 (CD54) in lymphoid malignancies are related to lineage derivation and stage of differentiation but not to tumor grade. *Leukemia.* 1991 5(10):848-53.
3. Bechter O E, Eisterer W, Thaler J, et. al. Expression of LFA-1 identifies different prognostic subgroups in patients with advanced follicle center lymphoma (FCL). *Leukemia Research.* 1999; 23(5):483-8.
4. Larson R. S, Davis T, Bolgna C, et. al. Dissociation of I Domain and global conformational changes in LFA-1: Refinement of small molecule-1 domain structure-activity relationships. *Biochemistry* in press.
5. Woska J R, Shih D, Taqueti V. R, Hogg N, Kelly T. A and Kishimoto K T. A small-molecule antagonist of LFA-1 blocks a conformational change important for LFA-1 function. *Journal of Leukocyte Biology.* 2001; 70:329-334.
6. Gursoy R. N and Siahaan T. J. Binding and internalization of an ICAM-1 peptide by the surface receptors of T-cells. *Journal of Peptide Research.* 1999; 53:414-421.
7. Hogg Nancy and Randi A. M. I Domain of $\beta_2$ Integrin Lymphocyte Function-associated Antigen-1 Contains a Binding Site for Ligand Intercellular Adhesion Molecule-1. *The Journal of Biological Chemistry.* 1994; 269(17): 12395-12398.
8. Kuriyama Y, Nakano M, Kawanishi Y and Toyama K. Cytofluorometric analysis of tumor cell size and follicle formation of B-cell lymphomas. *Rinsho Ketsueki.* 1995 36(4):279-285.
9. Petruzzelli L, Maduzia L and Springer T. A. Differential Requirements for LFA-1 Binding to ICAM-1 and LFA-1-Mediated Cell Aggregation. *The Journal of Immunology.* 1998; 160:4208-4216.
10. Buckley C. D, Ferguson E. D, Littler A. J, Bossy D and Simmons D L. Role of Ligands in the activation of LFA-1. *European Journal of Immunology.* 1997; 27:957-962.
11. Lub M, Kooyk Y and Figdor G. C. Ins and outs of LFA-1. *Immunology Today.* 1995; 16(10):479-483.
12. Kelly T. A, Jeanfavre, Mcneil W. D, Woska R. J and et. al. Cutting edge: A small molecule antagonist of LFA-1 mediated cell aadhesion. *The Journal of Immunology.* 1999: 5173-5177.
13. Last-Barney K, Davidson W, Cardozo M, Frye L L, Grygon C A, Hopkins J L, Jeanfavre D D, Pay S, Qian C, Stevenson J M, Tong L, Zindell R, Kelly T A. Binding site elucidation of hydantoin-based antagonists of LFA-1 using multidisciplinary technologies: evidence for the allosteric inhibition of a protein-protein interaction. *J Am Chem Soc.* 2001; 123(24):5643-5650.
14. Rocha M, Kruger A, Schirrmacher, et. al. Dynamic Expression Changes In Vivo of Adhesion and Costimulatory Molecules Determine Load and Pattern of Lymphoma Liver Metastasis. *Clinical Cancer Research.* 1996; 2:811-820.
15. Kang J H, Chung J K, Lee Y J, Shin J H, Jeong J M, Lee D S, Lee M C. Establishment of a human hepatocellular carcinoma cell line highly expressing sodium iodide symporter for radionuclide gene therapy. J Nucl Med. 2004; 45(9):1571-1576.
16. Norenberg J P, Krenning B J, Konings I R, De Jong M, Garmestani K, Brechbeil M W, Atcher R W, Kusewitt D F, Garmestani K, Brechbiel M W, Kvols L K. Safety and efficacy of 213Bi-[DOTA°,Tyr³]octreotide (Bi-DOTA-TOC) in peptide receptor radionuclide therapy (PRRT) of neuroendocrine tumors in a pre-clinical model. *Clinical Cancer Research*; November 2001; v7(11), suppl. S, p. 3732S.

17. Delcambre C, Reman O, Henry-Amar M, Peny A M, Macro M, Cheze S, et al. Clinical relevance of gallium-67 scintigraphy in lymphoma before and after therapy. Eur J Nucl Med 2000; 27(2):176-184.
18. Johnston G S, Go M F, Benua R S, Larson S M, Andrews G A, Hubner K F. Gallium-67 citrate imaging in Hodgkin's disease: final report of cooperative group. J Nucl Med 1977; 18(7):692-698.
19. Andrews G A, Hubner K F, Greenlaw R H. Ga-67 citrate imaging in malignant lymphoma: final report of cooperative group. 1978; 19(9):1013-1019.
20. Hussain R, Christie D R, Gebski V, Barton M B, Gruenewald S M. The role of the gallium scans in primary extranodal lymphoma. J Nucl Med 1998; 39(1):95-98.
21. Gallamini A, Biggi A, Fruterro A, Pugno F, Cavallero G, Pregno P, et al. Revisiting the prognoistic role of gallium scintigraphy in low-grade non-Hodgkin's lymphoma. Eur J Nucl Med 1997; 24(12):1499-1506.
22. Ben-Haim S, Bar-Shalom R, Israel O, Haim N, Epelbaum R, Ben-Shachar M, et al. Utility of gallium-67 sicntigraphy in low-grade non-Hodgkin's lymphoma. J Clin Oncol 1996; 14(6): 1936-1942.
23. Kumar R, Maillard I, Schuster S J, Alavi A. Utility of fluorodeoxyglucose-PET imaging in management of patients with Hodgkin's and non-Hodgkin's lymphomas. Radiol Clin N Am 2004; 42:1083-1100.
24. Macapinlac H A. The utility of 2-deoxy-2-[$^{18}$F]fluoro-d-glucose-positron emission tomography and combined positron emission tomography and computed tomography in lymphoma and melanoma. Molecular Imaging and Biology 2004; 6(4):200-2007.

The invention claimed is:

1. A method of diagnosing the existence of an infectious disease which is mediated through ICAM-1/LFA-1 receptors in tissue of a patient in which levels of said receptors are suspected of being elevated comprising administering to said patient an effective amount of at least one compound according to the following chemical structure:

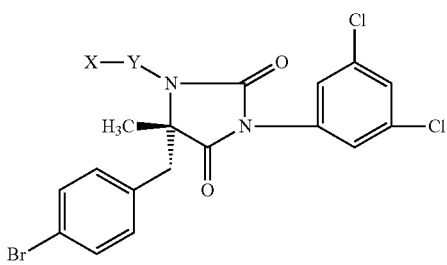

where Y is a chemical linker which links the nitrogen to a chelate group or tricarbonyl complex X, wherein X incorporates or complexes with a radioisotope, or a pharmaceutically acceptable salt thereof, measuring the amount of said compound which binds to said tissue in said patient, and comparing said measurement from said measuring step with a standard, wherein an elevated measurement in comparison to said standard is indicative of the existence of said infectious disease in said patient and said infectious disease is a skin or soft tissue infection, a bone or joint infection, a central nervous system infection, an upper or lower respiratory tract infection, infective endocarditis, tuberculosis, a gastrointestinal infection, an intra-abdominal infection, a parasitic infection, a urinary tract infection or a post-surgical infection.

2. The method according to claim 1 wherein said infectious disease is a central nervous system infection arising from meningococcal, pneumococcal, diplococcal, H. influenzae, Cryptococcal neoformans or viral encephalitis, bronchitis, bronchiolitis, pneumonia, otitis media, pharyngitis, sinusitis, epiglottitis, laryngitis, enterotoxigenic diarrhea, enterhemorrhagic diarrhea, travelers diarrhea, pseudomembranous colitis, Shigellosis, Salmonellosis, Campylobacteriosis, Yersinosis, gastroenteritis, peritonitis, abscess, a protozoal infection, a disease from a roundworm or a flatworm, pediculosis, acariasis, prostatitis, urethritis, epididymitis, cervicitis or vulvovaginitis, proctitis, salpingitis, histoplasmosis, blastomycosis, coccidiodomycosis, cryptococcosis, a post-surgical infection, folliculitis, furuncles, carbuncles, erysipelas, lymphangitis, cellulitis, a necrotizing soft tissue infection, a diabetic foot infection, decubitus ulcers, mastoiditis, osteomyelitis or infectious arthritis.

3. The method according to claim 1 wherein X incorporates a radioisotope selected from the group consisting of $^{90}$Y, $^{111}$In, $^{177}$Lu, $^{225}$Ac, $^{213}$Bi, $^{67}$Ga, $^{68}$Ga, $^{64}$Cu, $^{67}$Cu, $^{71}$As, $^{72}$As, $^{76}$As, $^{77}$As, $^{65}$Zn, $^{76}$Br, $^{48}$V, $^{49}$V, $^{203}$Pb, $^{209}$Pb, $^{212}$Pb, $^{166}$Ho, $^{153}$Pm, $^{201}$Tl, $^{188}$Re, $^{186}$Re, $^{99m}$Tc or a mixture thereof.

4. The method according to claim 1 wherein Y is a —(CH$_2$)$_n$Z— group where n is 4, Z is a NR group and R is H, and which group links the nitrogen of said NR group to a 1,4,7,10-tetraazacyclododecane-1,4,7,10-tetraacetic acid (DOTA) group and wherein said DOTA group incorporates or complexes with a radioisotope selected from the group consisting of $^{90}$Y, $^{111}$In, $^{177}$Lu, $^{67}$Ga, $^{68}$Ga, and $^{213}$Bi, or a pharmaceutically acceptable salt thereof.

5. The method according to claim 3 wherein said radioisotope is $^{90}$Y, $^{213}$Bi, $^{177}$Lu or $^{111}$In.

6. The method according to claim 3 wherein said radioisotope is $^{213}$Bi, $^{177}$Lu or $^{111}$In.

7. The method according to claim 3 wherein said radioisotope is $^{213}$Bi, $^{90}$Y, or $^{177}$Lu.

8. The method according to claim 3 wherein said radioisotope is $^{213}$Bi.

9. A method of monitoring the treatment of a ICAM-1/LFA-1 mediated infectious disease in tissue or inflamed tissues of a patient comprising administering to said patient undergoing a course of treatment for said disease an effective amount of at least one compound according to the chemical structure:

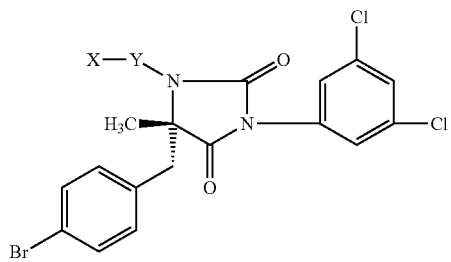

where Y is a chemical linker which links the nitrogen to a chelate group or tricarbonyl complex X, wherein X incorporates or complexes with a radioisotope, or a pharmaceutically acceptable salt thereof;

measuring the amount of said compound which binds to said tissue in said patient at two different times or more during treatment; and comparing the measurements obtained in said measuring step at said different times with a standard from uninfected tissue and/or infected tissue, wherein said measurements obtained from said patient are compared to said standard(s) and optionally, to each other, such that said comparison is indicative of the progress or absence of progress in the treatment of said infectious disease, wherein said infectious disease is a skin or soft tissue infection, a bone or joint infection, a central nervous system infection, an upper or lower respiratory tract infection, infective endocarditis, tuberculosis, a gastrointestinal infection, an intra-abdominal infection, a parasitic infection, a urinary tract infection or a post-surgical infection.

10. The method according to claim 9 wherein said infectious disease is a central nervous system infection arising from meningococcal, pneumococcal, diplococcal, *H. influenzae*, *Cryptococcal neoformans* or viral encephalitis, bronchitis, bronchiolitis, pneumonia, otitis media, pharyngitis, sinusitis, epiglottitis, laryngitis, enterotoxigenic diarrhea, enterohemorrhagic diarrhea, travelers diarrhea, pseudomembranous colitis, Shigellosis, Salmonellosis, Campylobacteriosis, Yersinosis, gastroenteritis, peritonitis, abscess, a protozoal infection, a disease from a roundworm or a flatworm, pediculosis, acariasis, prostatitis, urethritis, epididymitis, cervicitis or vulvovaginitis, proctitis, salpingitis, histoplasmosis, blastomycosis, coccidiodomycosis, cryptococcosis, a post-surgical infection, folliculitis, furuncles, carbuncles, erysipelas, lymphangitis, cellulitis, a necrotizing soft tissue infection, a diabetic foot infection, decubitus ulcers, mastoiditis, osteomyelitis or infectious arthritis.

11. The method according to claim 10 wherein X incorporates a radioisotope selected from the group consisting of $^{90}$Y, $^{111}$In, $^{177}$Lu, $^{225}$Ac, $^{213}$Bi, $^{67}$Ga, $^{68}$Ga, $^{64}$Cu, $^{67}$Cu, $^{71}$As, $^{72}$As, $^{76}$As, $^{77}$As, $^{65}$Zn, $^{76}$Br, $^{48}$V, $^{49}$V, $^{203}$Pb, $^{209}$Pb, $^{212}$Pb, $^{166}$Ho, $^{153}$Pm, $^{201}$Tl, $^{188}$Re, $^{186}$Re, $^{99m}$Tc or a mixture thereof.

12. The method according to claim 10 wherein Y is a —(CH$_2$)$_n$Z— group where n is 4, Z is a NR group and R is H, and which group links the nitrogen of said NR group to a 1,4,7,10-tetraazacyclododecane-1,4,7,10-tetraacetic acid (DOTA) group X and wherein said DOTA group incorporates or complexes with a radioisotope selected from the group consisting of $^{90}$Y, $^{111}$In, $^{177}$Lu, $^{67}$Ga, $^{68}$Ga, and $^{213}$Bi, or a pharmaceutically acceptable salt thereof.

13. The method according to claim 12 wherein said radioisotope is $^{90}$Y, $^{213}$Bi, $^{177}$Lu or $^{111}$In.

14. The method according to claim 12 wherein said radioisotope is $^{213}$Bi, $^{177}$Lu or $^{111}$In.

15. The method according to claim 12 wherein said radioisotope is $^{213}$Bi, $^{90}$Y, or $^{177}$Lu.

16. The method according to claim 12 wherein said radioisotope is $^{213}$Bi.

17. The method according to claim 10 wherein said therapy is modified after said monitoring.

18. A method of treating and monitoring an ICAM-1/LFA-1 mediated infectious disease in tissue or inflamed tissues of a patient comprising treating said disease in said patient and during said treating of said disease, administering to said patient an effective amount of at least one compound according to the chemical structure:

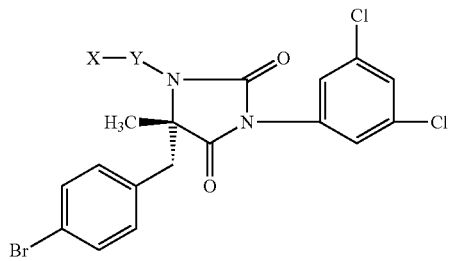

where Y is a chemical linker which links the nitrogen to a chelate group or tricarbonyl complex X, wherein X incorporates or complexes with a radioisotope, or a pharmaceutically acceptable salt thereof; and measuring the amount of said compound which binds to said tissue in said patient at different times during said treatment and comparing the measurements obtained in said measuring step a$_t$ said different times with a standard from infected tissue, wherein said measurements obtained from said patient are compared to said standard(s) and optionally, to each other, such that said comparison is indicative of the progress or absence of progress in the treatment of said infectious disease, wherein said infectious disease is a skin or soft tissue infection, a bone or joint infection, a central nervous system infection, an upper or lower respiratory tract infection, infective endocarditis, tuberculosis, a gastrointestinal infection, an intra-abdominal infection, a parasitic infection, a urinary tract infection or a post-surgical infection.

19. The method according to claim 18 wherein said infectious disease is a central nervous system infection arising from meningococcal, pneumococcal, diplococcal, *H. influenzae*, *Cryptococcal neoformans* or viral encephalitis, bronchitis, bronchiolitis, pneumonia, otitis media, pharyngitis, sinusitis, epiglottitis, laryngitis, enterotoxigenic diarrhea, enterohemorrhagic diarrhea, travelers diarrhea, pseudomembranous colitis, Shigellosis, Salmonellosis, Campylobacteriosis, Yersinosis, gastroenteritis, peritonitis, abscess, a protozoal infection, a disease from a roundworm or a flatworm, pediculosis, acariasis, prostatitis, urethritis, epididymitis, cervicitis or vulvovaginitis, proctitis, salpingitis, histoplasmosis, blastomycosis, coccidiodomycosis, cryptococcosis, a post-surgical infection, folliculitis, furuncles, carbuncles, erysipelas, lymphangitis, cellulitis, a necrotizing soft tissue infection, a diabetic foot infection, decubitus ulcers, mastoiditis, osteomyelitis or infectious arthritis.

20. The method according to claim 18 wherein X incorporates a radioisotope selected from the group consisting of $^{90}$Y, $^{111}$In, $^{177}$Lu, $^{225}$Ac, $^{213}$Bi, $^{67}$Ga, $^{68}$Ga, $^{64}$Cu, $^{67}$Cu, $^{71}$As, $^{72}$As, $^{76}$As, $^{77}$As, $^{65}$Zn, $^{76}$Br, $^{48}$V, $^{49}$V, $^{203}$Pb, $^{209}$Pb, $^{212}$Pb, $^{166}$Ho, $^{153}$Pm, $^{201}$Tl, $^{188}$Re, $^{186}$Re, $^{99m}$Tc or a mixture thereof.

21. The method according to claim 20 wherein at least one of said times of measuring said amount of said compound which binds to said tissue in said patient is at the beginning of said treatment.

22. The method according to claim 18 wherein Y is a —(CH$_2$)$_n$Z— group where n is 4, Z is a NR group and R is H, and which group links the nitrogen of said NR group to a 1,4,7,10-tetraazacyclododecane-1,4,7,10-tetraacetic acid (DOTA) group X and wherein said DOTA group incorporates or complexes with a radioisotope selected from the group consisting of $^{90}$Y, $^{111}$In, $^{177}$Lu, $^{67}$Ga, $^{68}$Ga, and $^{213}$Bi, or a pharmaceutically acceptable salt thereof.

23. The method according to claim 21 wherein Y is a —$(CH_2)_nZ$— group where n is 4, Z is a NR group and R is H, and which group links the nitrogen of said NR group to a 1,4,7,10-tetraazacyclododecane-1,4,7,10-tetraacetic acid (DOTA) group X and wherein said DOTA group incorporates or complexes with a radioisotope selected from the group consisting of $^{90}Y$, $^{111}In$, $^{177}Lu$, $^{67}Ga$, $^{68}Ga$, and $^{213}Bi$, or a pharmaceutically acceptable salt thereof.

24. The method according to claim 23 wherein said radioisotope is $^{90}Y$, $^{213}Bi$, $^{177}Lu$ or $^{111}In$.

25. The method according to claim 23 wherein said radioisotope is $^{213}Bi$, $^{177}Lu$ or $^{111}In$.

26. The method according to claim 23 wherein said radioisotope is $^{213}Bi$, $^{90}Y$, or $^{177}Lu$.

27. The method according to claim 23 wherein said radioisotope is $^{213}Bi$.

28. The method according to claim 23 wherein said therapy is modified after said monitoring.

29. The method according to claim 28 wherein said radioisotope is $^{90}Y$, $^{213}Bi$, $^{177}Lu$ or $^{111}In$.

30. The method according to claim 28 wherein said radioisotope is $^{213}Bi$, $^{177}Lu$ or $^{111}In$.

31. The method according to claim 28 wherein said radioisotope is $^{213}Bi$, $^{90}Y$, or $^{177}Lu$.

32. The method according to claim 28 wherein said radioisotope is $_{213}Bi$.

33. The method according to claim 19 wherein said therapy is modified after said monitoring.

* * * * *